US012447086B1

(12) United States Patent
Davis, III et al.

(10) Patent No.: US 12,447,086 B1
(45) Date of Patent: Oct. 21, 2025

(54) SYSTEM, APPARATUS, AND METHOD FOR INFANT INCUBATION

(71) Applicants: MediCradle Foundation, Richmond, VA (US); ILJ Corporation, North Chesterfield, VA (US)

(72) Inventors: John Merrill Davis, III, Midlothian, VA (US); Jane Dornbusch Davis, Midlothian, VA (US); Mark Wayne Kitchen, Henrico, VA (US); John David Keltonic, North Chesterfield, VA (US)

(73) Assignees: MediCradle Foundation, Richmond, VA (US); ILJ Corporation, North Chesterfield, VA (US)

( * ) Notice: Subject to any disclaimer, the term of this patent is extended or adjusted under 35 U.S.C. 154(b) by 0 days.

(21) Appl. No.: 18/934,834

(22) Filed: Nov. 1, 2024

(51) Int. Cl.
*A61G 11/00* (2006.01)
*A61M 16/10* (2006.01)

(52) U.S. Cl.
CPC ......... *A61G 11/00* (2013.01); *A61M 16/1075* (2013.01); *A61G 2210/90* (2013.01); *A61M 2205/3334* (2013.01); *A61M 2205/362* (2013.01); *A61M 2205/75* (2013.01)

(58) Field of Classification Search
CPC ............... A61G 11/00; A61G 2210/90; A61M 16/1075; A61M 2205/3334; A61M 2205/362; A61M 2205/75
See application file for complete search history.

(56) References Cited

U.S. PATENT DOCUMENTS

2004/0133064 A1* 7/2004 Castillon Levano .. A61G 11/00 600/22
2021/0283357 A1* 9/2021 Leonard ............ A61M 16/1005
2024/0076600 A1* 3/2024 Watanabe .............. C12M 23/38

OTHER PUBLICATIONS

Webpage from website created by inventor having information provided by the inventor, available as of Jun. 10, 2023, at https://medicradle.org/ (3 pages).

* cited by examiner

*Primary Examiner* — Carrie R Dorna
*Assistant Examiner* — Joshua Daryl D Lannu
(74) *Attorney, Agent, or Firm* — Keefe IP Law, PLLC

(57) ABSTRACT

An incubator is disclosed. The incubator has an insulated housing that forms an incubation chamber, a plurality of recirculating heating airflow passages configured to draw a heating airflow from the incubation chamber, heat the heating airflow, and return the heating airflow to the incubation chamber, and a plurality of ventilation airflow passages configured to draw a ventilation airflow from outside of the incubator and into the incubation chamber, and vent the ventilation airflow out of the incubation chamber. The plurality of recirculating heating airflow passages are separate from the plurality of ventilation airflow passages.

20 Claims, 13 Drawing Sheets

SYSTEM, APPARATUS, AND METHOD FOR INFANT INCUBATION

TECHNICAL FIELD

The present disclosure generally relates to a system, apparatus, and method for incubation, and more particularly to a system, apparatus, and method for infant incubation.

BACKGROUND

The vast majority of incubators are designed for use in environments that have reliable electrical power access and that are highly sanitary. For example, incubators are typically designed for use in hospital settings including extremely reliable electrical systems and sanitary standards.

In contrast, many areas of the developing world face significant challenges regarding infant mortality. Increased availability of infant incubation would significantly contribute to a decline in the relatively high infant mortality crisis facing these parts of the world. As most conventional incubators are designed for hospitals in developed countries, these incubators are often a poor fit for conditions in many parts of the developing world.

For example, a need for effective incubation exists in developing areas of the world that struggle with electrical power access and that lack facilities with high degrees of sanitation. Much of the developing world lacks the type of developed world hospital settings for which incubators are typically designed. Attempting to use typical incubators, which are designed for hospitals in the developed world, in the developing world typically results in these incubators performing poorly due to their relatively high electrical demands and high sanitary criteria not being adequately met by most facilities in the developing worlds. That is, typical incubators use too much power and are too susceptible to malfunctioning due to poor sanitation conditions to perform well in the existing conditions in medical facilities in the developing world.

Accordingly, a need in the art exists for infant incubation that can perform well in facilities having unreliable electrical power access and challenging sanitary conditions.

The exemplary disclosed system, apparatus, and method of the present disclosure are directed to overcoming one or more of the shortcomings set forth above and/or other deficiencies in existing technology.

SUMMARY OF THE DISCLOSURE

In one exemplary aspect, the present disclosure is directed to an incubator. The incubator includes an insulated housing that forms an incubation chamber, a plurality of recirculating heating airflow passages configured to draw a heating airflow from the incubation chamber, heat the heating airflow, and return the heating airflow to the incubation chamber, and a plurality of ventilation airflow passages configured to draw a ventilation airflow from outside of the incubator and into the incubation chamber, and vent the ventilation airflow out of the incubation chamber. The plurality of recirculating heating airflow passages are separate from the plurality of ventilation airflow passages.

In another aspect, the present disclosure is directed to an incubator. The incubator includes an exterior housing assembly, an interior housing assembly, and an insulation layer disposed between the exterior housing assembly and the interior housing assembly. The interior housing assembly, the insulation layer, and the exterior housing assembly form an insulated housing that forms an incubation chamber. The exterior housing assembly and the interior housing assembly are formed from a plastic material.

DETAILED DESCRIPTION AND INDUSTRIAL APPLICABILITY

Figure 1:
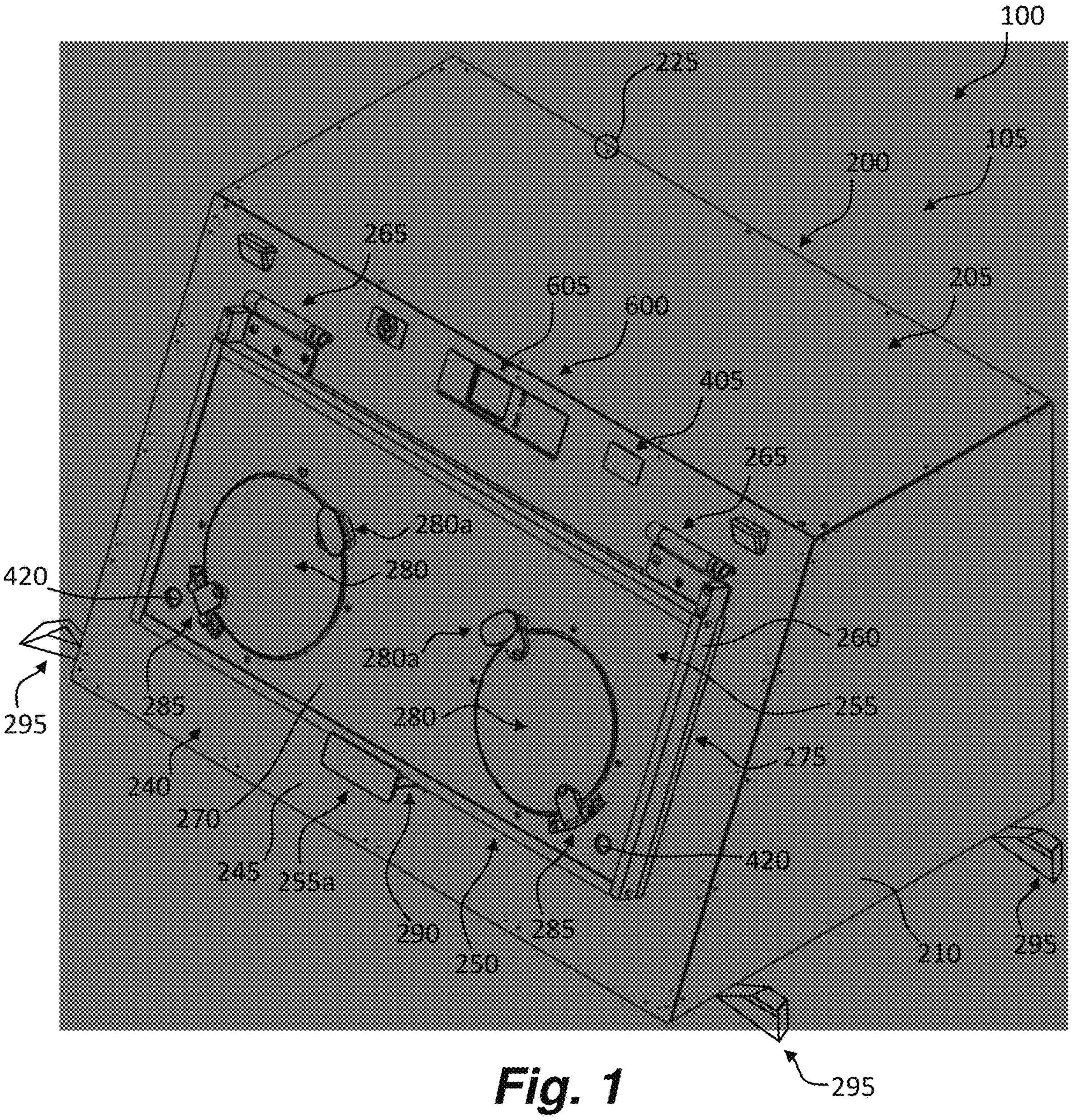
FIG. 1 is a perspective view of an exemplary embodiment of the present invention.

The exemplary disclosed system, apparatus, and method may provide incubation (e.g., infant incubation). FIG. 1 illustrates an exemplary disclosed incubation system 100 that may include an incubator 105 for providing incubation for an infant. Incubator 105 may include a structural and insulation system 200 that may structurally support a heating system 300, a ventilation system 400, a skin sensor system 500, a control system 600, and a power system 700. Control system 600 and power system 700 may control and power heating system 300, ventilation system 400, and skin sensor system 500.

As illustrated in FIGS. 1 through 5, structural and insulation system 200 may include an insulated housing 205 that may include an exterior housing assembly 210, an insulation layer 215, and an interior housing assembly 220. Insulation layer 215 may be disposed between some or substantially all portions of exterior housing assembly 210 and interior housing assembly 220.

Figure 2:
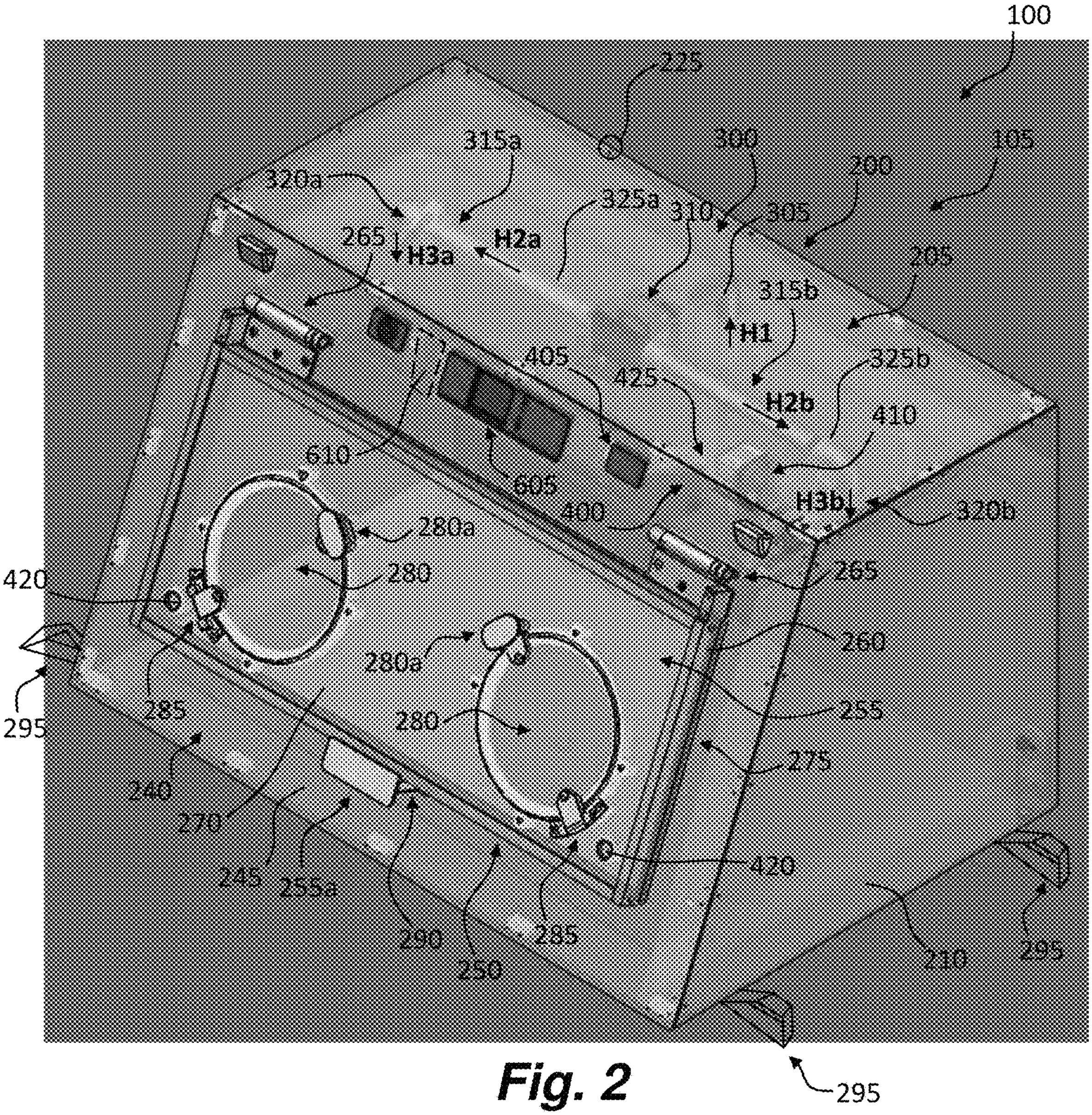
FIG. 2 is another perspective view of the exemplary embodiment of the present invention illustrated in FIG. 1.
Figure 2A:
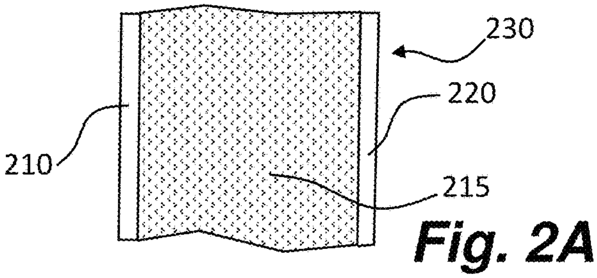
FIG. 2A is a sectional view of an exemplary embodiment of the present invention.
Figure 3:
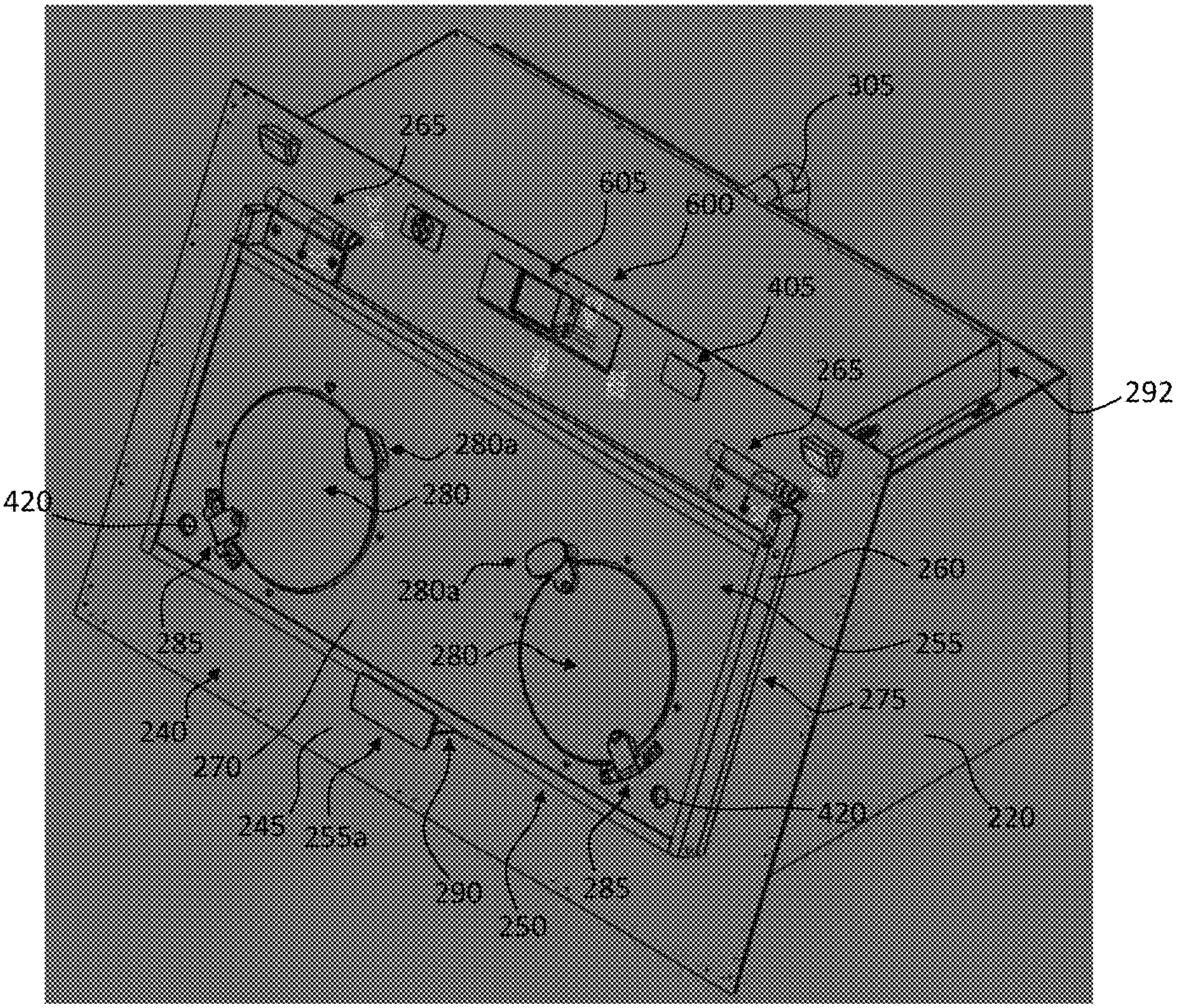
FIG. 3 is another perspective view of the exemplary embodiment of the present invention illustrated in FIG. 1.
Figure 4:
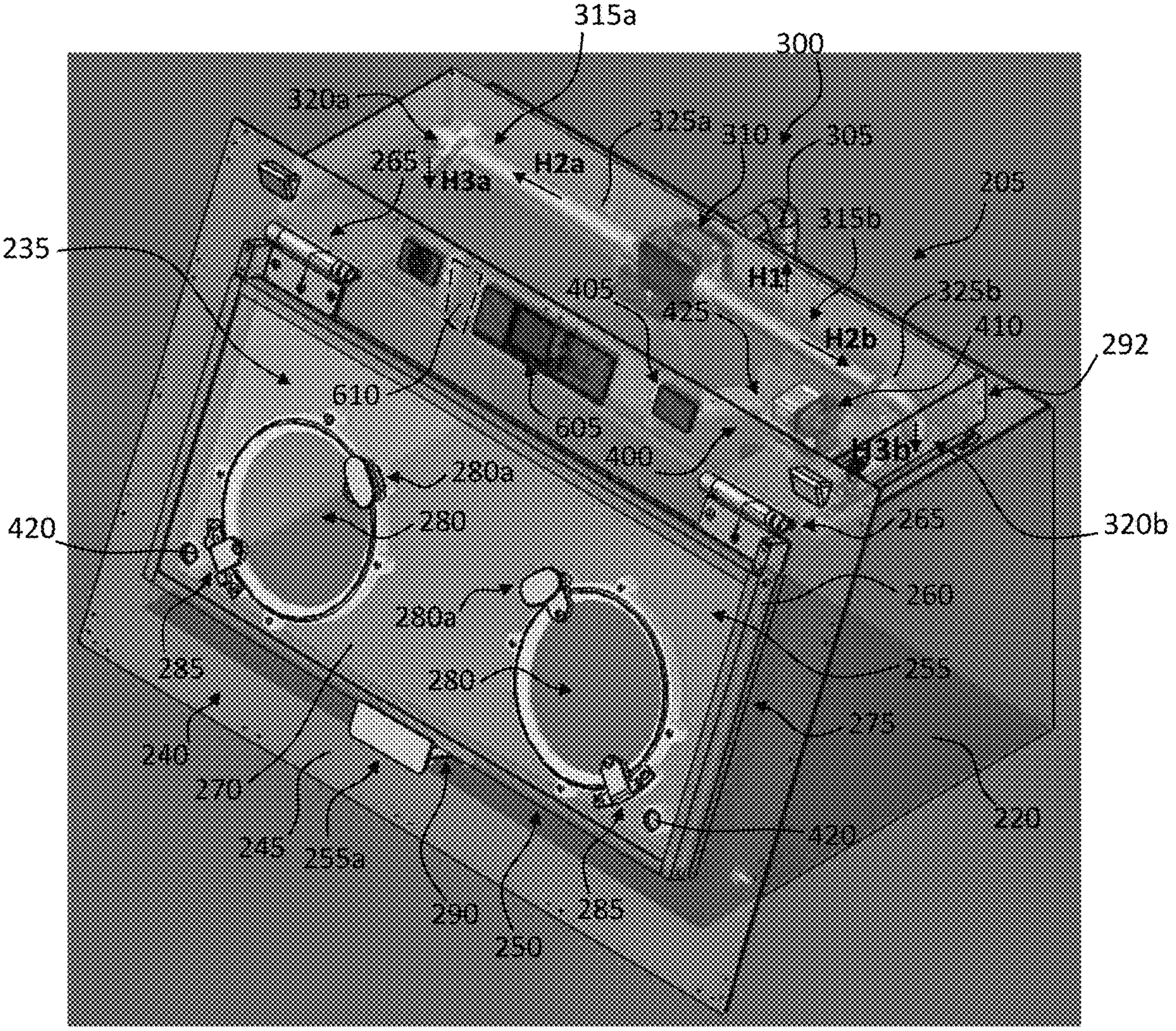
FIG. 4 is another perspective view of the exemplary embodiment of the present invention illustrated in FIG. 1.
Figure 5:
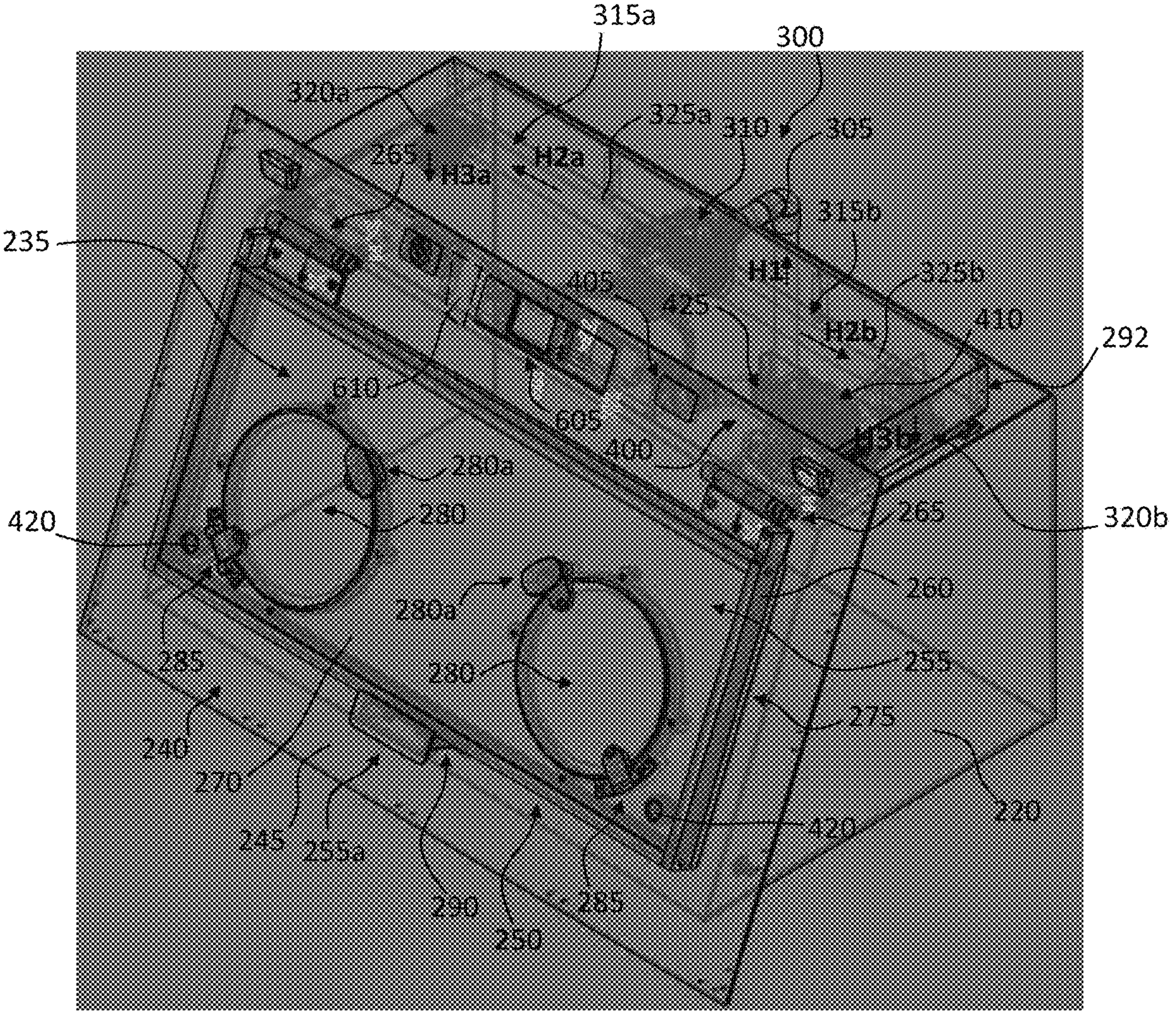
FIG. 5 is another perspective view of the exemplary embodiment of the present invention illustrated in FIG. 1.

As illustrated in FIGS. 1, 2, and 2A, exterior housing assembly 210 may include a plurality of structural members that may be integrally formed and/or attached together via welding, mechanical fasteners such as bolts and/or screws, and/or any other suitable attachment technique. For example, exterior housing assembly 210 may be attached together by a plurality of fasteners 225 such as, for example, screws, bolts, staples, rivets, and/or any other suitable fastener. Fasteners 225 may for example fasten members of exterior housing assembly 210 to members of insulation layer 215 and/or interior housing assembly 220. Exterior housing assembly 210 may include structural plates, structural angles, structural channels, and/or any other suitable shapes. Exterior housing assembly 210 may be formed from structural plastic, metal, wood, composite material, and/or any other suitable structural material. For example, exterior housing assembly 210 may be formed from a thermoplastic polymeric material. Exterior housing assembly 210 may be formed from HDPE, polyvinyl chloride material, acrylonitrile butadiene styrene (ABS) material, polycarbonate material, PPS material, Polypropylene, and/or any other suitable structural material. In at least some exemplary embodiments, exterior housing assembly 210 may be formed from relatively thin HDPE plates or sheet members (e.g., of a thickness between about 1/16" and about 3/4" or more, between about 1/16" and about 1/2", between about 1/16" and about 1/4", between about 1/16" and about 1/8", or any other suitable thickness).

As illustrated in FIGS. 2A and 3-5, interior housing assembly 220 may include a plurality of structural members that may be formed from similar material as members of exterior housing assembly 210 and attached together similarly to members of exterior housing assembly 210, for example as described above. Interior housing assembly 220 may be configured generally similarly to and sized slightly smaller than exterior housing assembly 210, so that interior housing assembly 220 may fit within exterior housing assembly 210, with a gap 230 formed between exterior housing assembly 210 and interior housing assembly 220.

Insulation layer 215 may be disposed in gap 230 so that insulation layer 215 is sandwiched between exterior housing assembly 210 and interior housing assembly 220. Insulation layer 215 may be formed from any suitable insulation material having a relatively low thermal conductivity. Insulation layer 215 may be formed from foam, mineral wool, perlite, polyurethane, polystyrene, cellulose, fiber material (e.g., natural fiber), air (e.g., gap 230 may be partially or substantially entirely empty), and/or any other suitable insulative material. For example, insulation layer 215 may be formed from closed cell foam or foam cell material. In at least some exemplary embodiments, insulation layer 215 may be formed from foam material such as polyethylene foam, polyurethane foam, neoprene foam, latex foam, gel foam, and/or any other suitable type of foam. Insulation layer 215 may have any suitable thickness such as, for example, between about 1/2" and about 4", between about 1" and about 3", between about 1.5" and about 2.5", between about 1.75" and about 2.5", or any other suitable thickness (e.g., about 2").

As illustrated in FIG. 2A, insulated housing 205 may be comprised of a composite structure of insulation layer 215 disposed (e.g., packed or sandwiched) between exterior housing assembly 210 and interior housing assembly 220. Insulated housing 205 may thereby be a relatively light, structurally rigid (e.g., structurally strong and/or robust), and insulative housing. In at least some exemplary embodiments, insulated housing 205 may include insulation layer 215 that may be foam disposed between exterior housing assembly 210 and interior housing assembly 220 that may be thermoplastic sheets (e.g., HDPE sheets), which may reduce an overall weight of incubator 105. Insulated housing 205 having insulation layer 215 disposed between exterior housing assembly 210 and interior housing assembly 220 may form an incubation chamber 235 in which an infant to be incubated may be placed (e.g., received). Insulated housing 205 having insulation layer 215 disposed between exterior housing assembly 210 and interior housing assembly 220 may form a top, bottom, sides (e.g., left and right sides), and back of incubation chamber 235. A front assembly 240 (e.g., described below) of structural and insulation system 200 may form an insulated front to incubation chamber 235. Insulated housing 205 and front assembly 240 may thereby together help to insulate incubation chamber 235.

Front assembly 240 may include a front member 245 that may be formed from similar material as exterior housing assembly 210 and interior housing assembly 220. Front assembly 240 may have a thickness that may be similar to or thicker (e.g., between 1/16" and 1/8" or 1/4" thicker) than exterior housing assembly 210 and interior housing assembly 220. Front assembly 240 may include a door aperture 250 for receiving a door assembly 255. Door aperture 250 may be selectively entirely and/or partially blocked or unblocked (e.g., opened) based on an operation of door assembly 255 for example as described below.

As illustrated in FIGS. 1 through 5, door assembly 255 may include a door frame 260 that may include a plurality of structural door members that may be attached together via the exemplary disclosed attachment techniques and/or integrally formed together as a single frame. Door frame 260 may be attached to front member 245 via one or more (e.g., a plurality of) door connectors 265 that may be any suitable movable assemblies such as hinges (e.g., mechanical hinges), slidable mechanical assemblies, removably attachable connectors, and/or any other suitable type of connector. In at least some exemplary embodiments, door connector 265 may be a sprung hinge (e.g., similar to a fire-door sprung hinge) that may hold door assembly 255 in position (e.g., open in position) when raised. For example, door connector 265 may be any suitable mechanical hinge to provide force to counteract a weight of door assembly 255. A user such as a caretaker (e.g., a nurse) may thereby relatively easily open and close the exemplary disclosed door with one hand, which may make care of an infant being incubated by incubator 105 easier.

Door assembly 255 may receive and support a plurality of door members 270. For example, door assembly 255 may include two door members 270 (e.g., or more than two door members 270) that may be supported by door frame 260 so that door members 270 are spaced from each other (e.g., so that a gap such as an air gap is formed between door members 270, the air gap being sealed by door frame 260). Door members 270 may thereby provide a double-wall front door. Door members 270 may be formed from plastic material (e.g., or glass material). Door members 270 may be formed from any suitable substantially transparent material (e.g., fully transparent material) and/or translucent material (e.g., to form a clear double-wall door). For example, door members 270 may be formed from acrylic, polycarbonate, PVC, PETG, and/or any other similar material. In at least some exemplary embodiments, door members 270 may be formed from any suitable transparent, plastic structural material.

A seal 275 including one or more seal members, which may be attached together via the exemplary disclosed attachment techniques or integrally formed into a single seal member, may be attached to door frame 260. Seal 275 may be disposed between door assembly 255 and front member 245 when door assembly 255 is closed to substantially block access to incubation chamber 235 and seal incubation chamber 235. Seal 275 may be formed from any suitable material for forming a substantially air-tight (e.g., fully air-tight) seal such as, for example, foam, silicone, natural rubber, synthetic rubber, fluoroplastic material, polyurethane, neoprene, and/or any other suitable sealing material. For example, seal 275 may be formed from any suitable flexible and/or elastic material. In at least some exemplary embodiments, seal 275 may be formed from a viscoelastic foam material such as, for example, memory foam including polyurethane material. Seal 275 may allow components used during medical care such as, for example, tubes and wires (e.g., of devices used for infant care) to reach an infant disposed in incubation chamber 235 from outside of incubator 105 without compromising integrity of incubator 105 against insects and other external and/or environmental threats.

Door members 270 may include one or more sets of aligned apertures (e.g., two or more sets of aligned apertures) that may each receive an access door 280. Access door 280 may be formed generally similarly to as described above regarding door assembly 255 (e.g., may include one or more door members generally similar to door members 270 that may form a transparent double wall). Access door 280 may be formed from similar material as door members 270 and may provide one or more transparent doors. Access door 280 may be attached to door members 270 using a door connector 285 that may be generally similar to door connector 265 (e.g., including the exemplary disclosed sprung hinge described above). Opening and closing one or more access doors 280 may provide access to an infant being cared for in incubation chamber 235 without opening entire door assembly 255. This may maintain better insulation, save power, and preserve seal 275 and door assembly 255 for when a smaller access aperture may be suitable for a given task such as making an adjustment in incubation chamber 235 (e.g., as opposed to complete access for placing and removing an infant in incubation chamber 235). Access door 280 may include a simplified connection (e.g., via a small number of fasteners such as two screws or bolts) to allow for easy replacement of an old or inoperable access door 285 with a new access door 285 by an end user of incubator 105.

Figure 9:
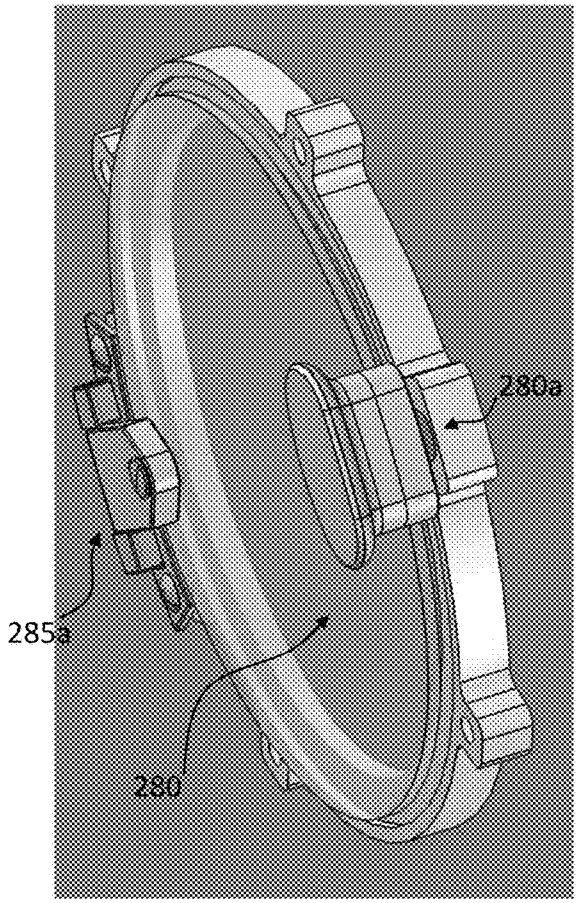
FIG. 9 is a detailed, perspective view of an exemplary embodiment of the present invention.
Figure 10:
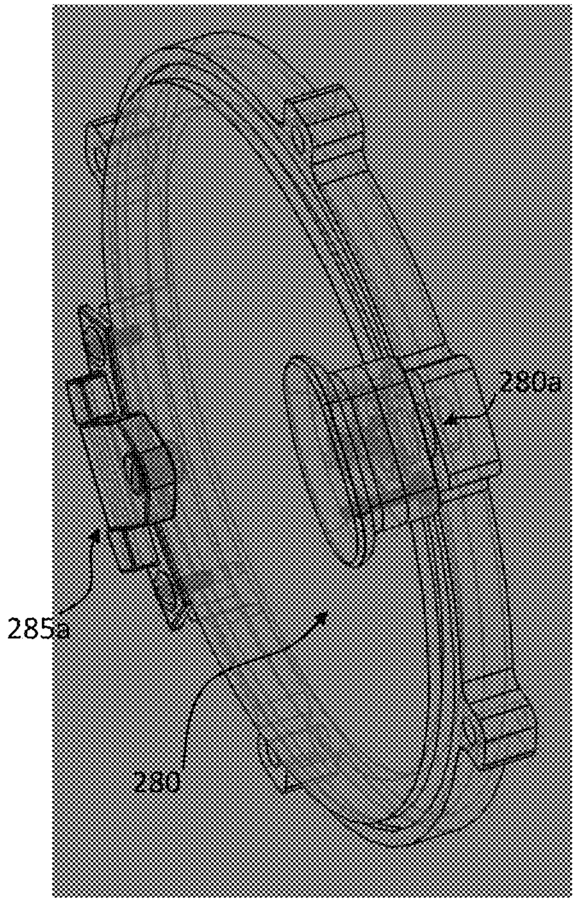
FIG. 10 is another detailed, perspective view of the exemplary embodiment of the present invention illustrated in FIG. 9.
Figure 11:
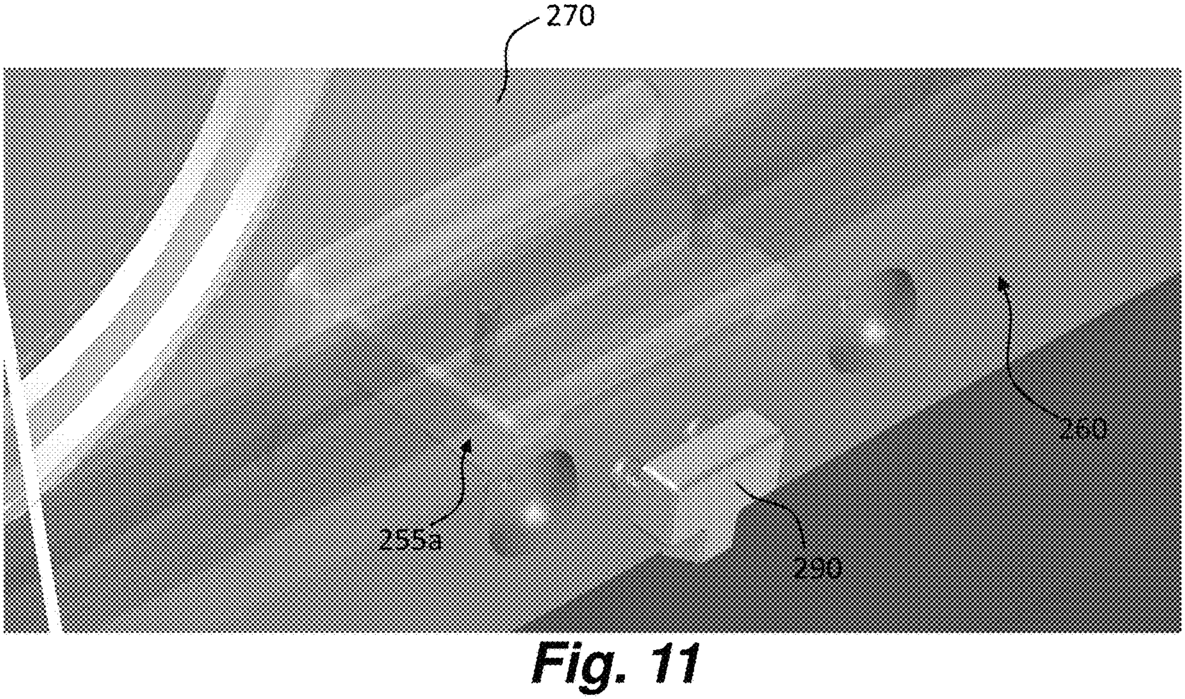
FIG. 11 is a detailed, perspective view of an exemplary embodiment of the present invention.
Figure 12:
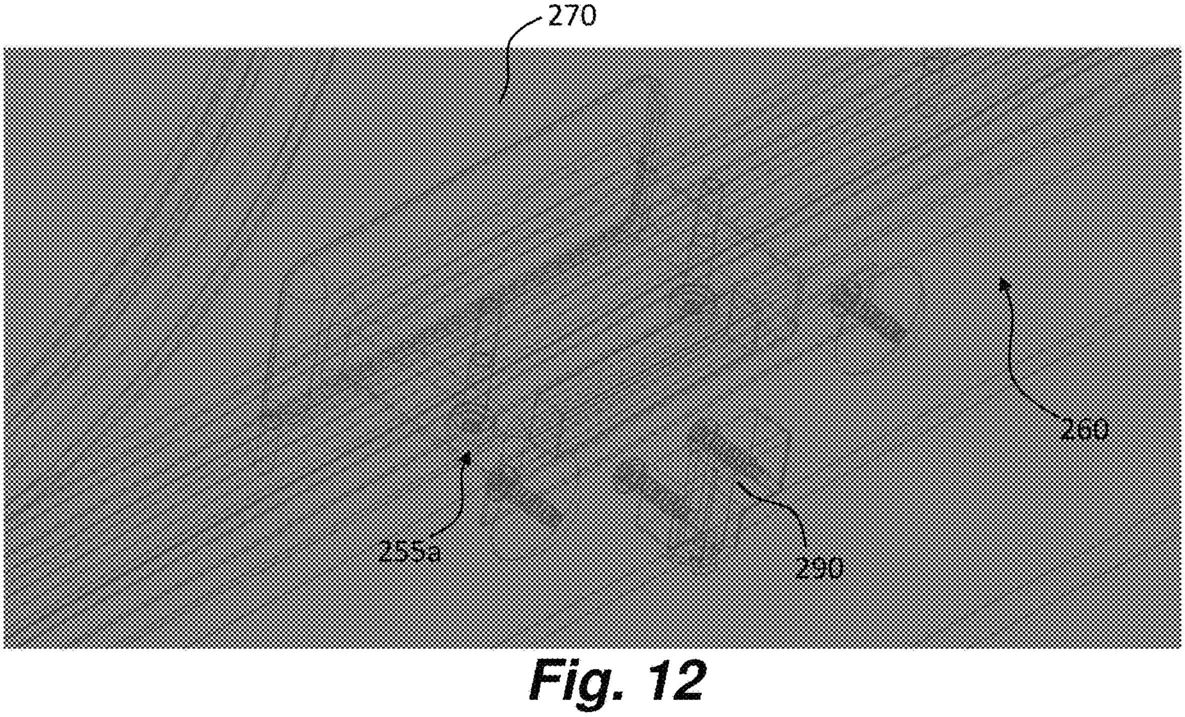
FIG. 12 is another detailed, perspective view of the exemplary embodiment of the present invention illustrated in FIG. 11.

Door assembly 255 and/or access doors 280 may include respective magnetic catch assemblies 255*a* and 280*a*, as illustrated in FIGS. 1-5. Magnetic catch assemblies 255*a* and 280*a* may be resilient assemblies including one or more magnets configured to be removably magnetically attached to a magnetic component (e.g., a metal component) to provide a magnetic catch or latch, which may be relatively unlikely to fail. Magnetic catch assemblies 255*a* and 280*a* may also facilitate a one-hand operation of door assembly 255 and/or access doors 280 further to as described above (e.g., regarding the exemplary disclosed sprung hinges). Magnetic catch assemblies 255*a* and 280*a* may include magnets formed from any suitable magnetic material such as, for example, ceramic magnetic materials (e.g., samarium cobalt magnetic materials), ferrite magnetic materials, alnico magnetic materials, and/or neodymium magnetic materials. Any other suitable catch or latch (e.g., mechanical latch) may also be used. FIGS. 9 and 10 illustrate an exemplary detailed view of access door 280 and magnetic catch assembly 280*a*. FIGS. 11 and 12 illustrate an exemplary detailed view of magnetic catch assembly 255*a*.

Returning to FIGS. 1 through 5, a magnetic sensor 290 may also be disposed at magnetic catch assembly 255*a* (e.g., and/or magnetic catch assembly 280*a*). Magnetic sensor 290 may be any suitable type of contact sensor that may sense whether or not door assembly 255 (e.g., and/or access door 280) is open or closed. Magnetic sensor 290 may include a reed switch, a magnetic proximity sensor, and/or any other suitable magnetic contact sensor (e.g., high reliability magnetic door sensor). Magnetic sensor 290 may communicate with the exemplary disclosed controller described below. FIGS. 11 and 12 illustrate an exemplary detailed view of magnetic sensor 290.

Insulated housing 205, door assembly 255, and one or more access doors 280 of structural and insulation system 200 may provide desired structural support and insulation to incubator 105. The exemplary disclosed insulation members and insulated doors (e.g., multiple or double layer doors) of structural and insulation system 200 described above may facilitate operation of incubator 105 at a relatively low power (e.g., operation at 150 Watts or less, or 100 Watts or less, which is significantly lower than incubators designed for developed world hospital use). Incubator 105 may thereby operate on a relatively low power battery (e.g., 12V lead-acid battery) when power may fail (e.g., when grid power fails).

Figure 6:
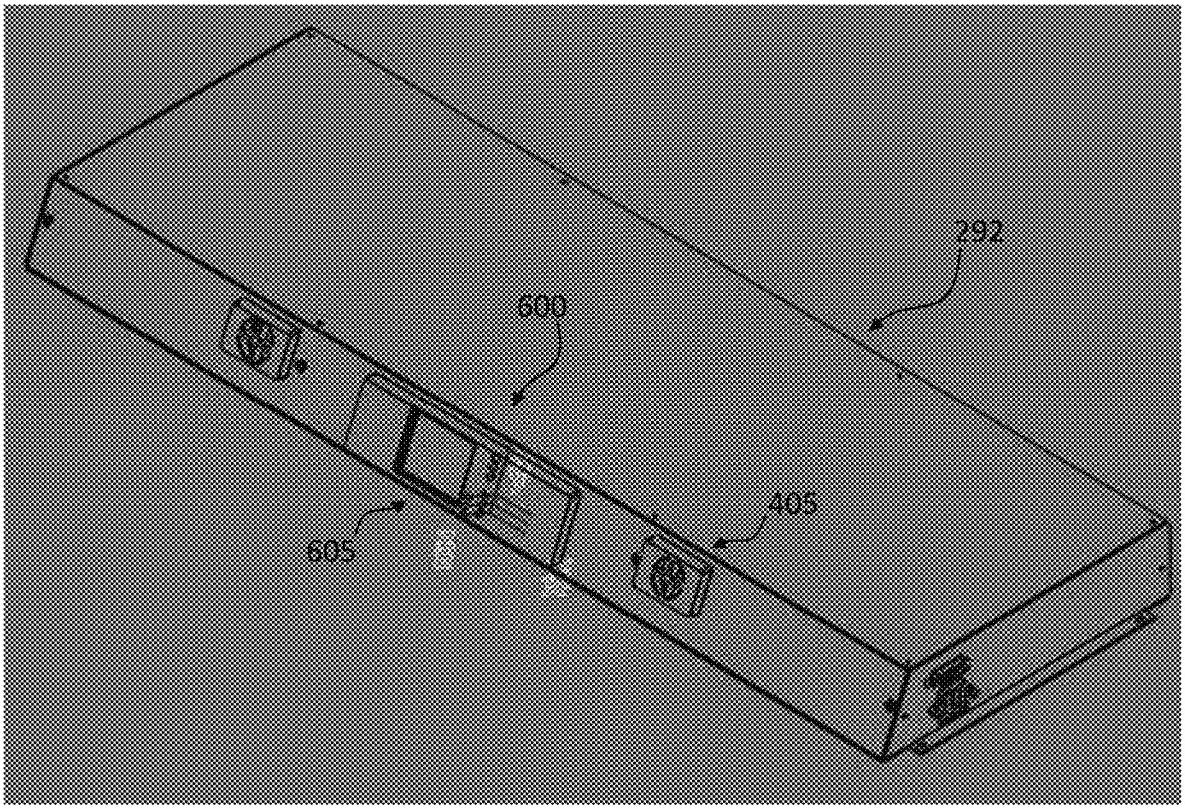
FIG. 6 is a detailed, perspective view of an exemplary embodiment of the present invention.
Figure 7:
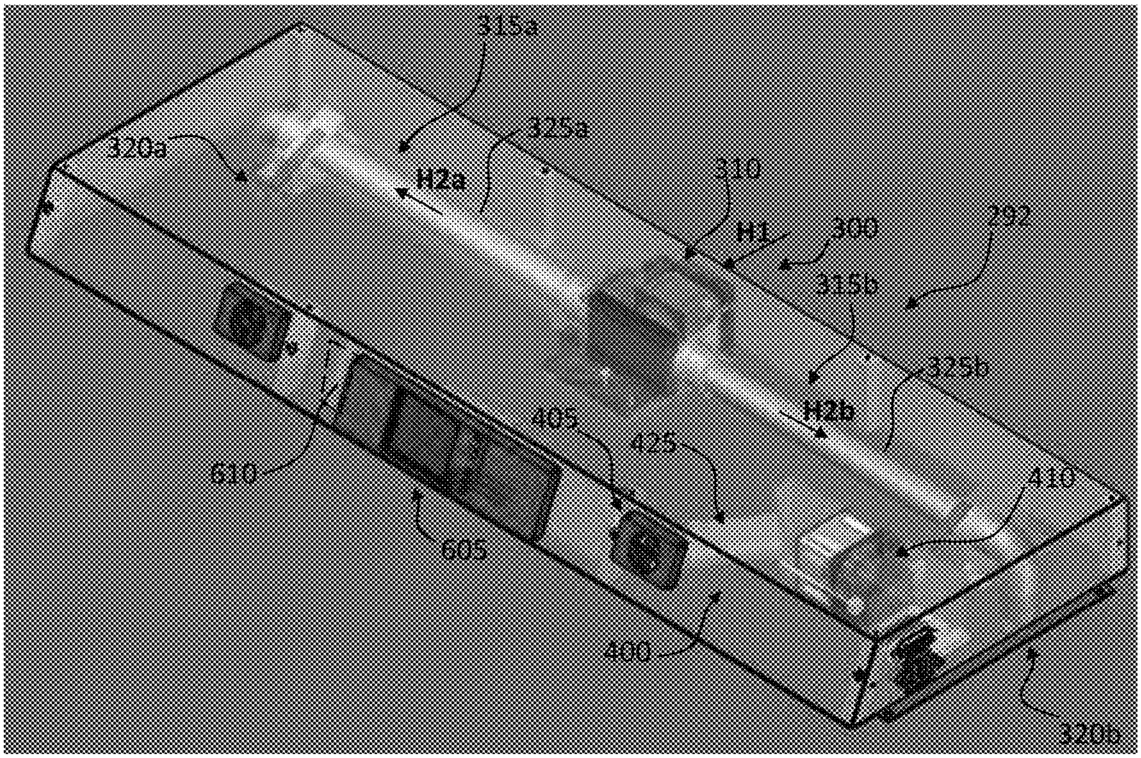
FIG. 7 is another detailed, perspective view of the exemplary embodiment of the present invention illustrated in FIG. 6.
Figure 8:
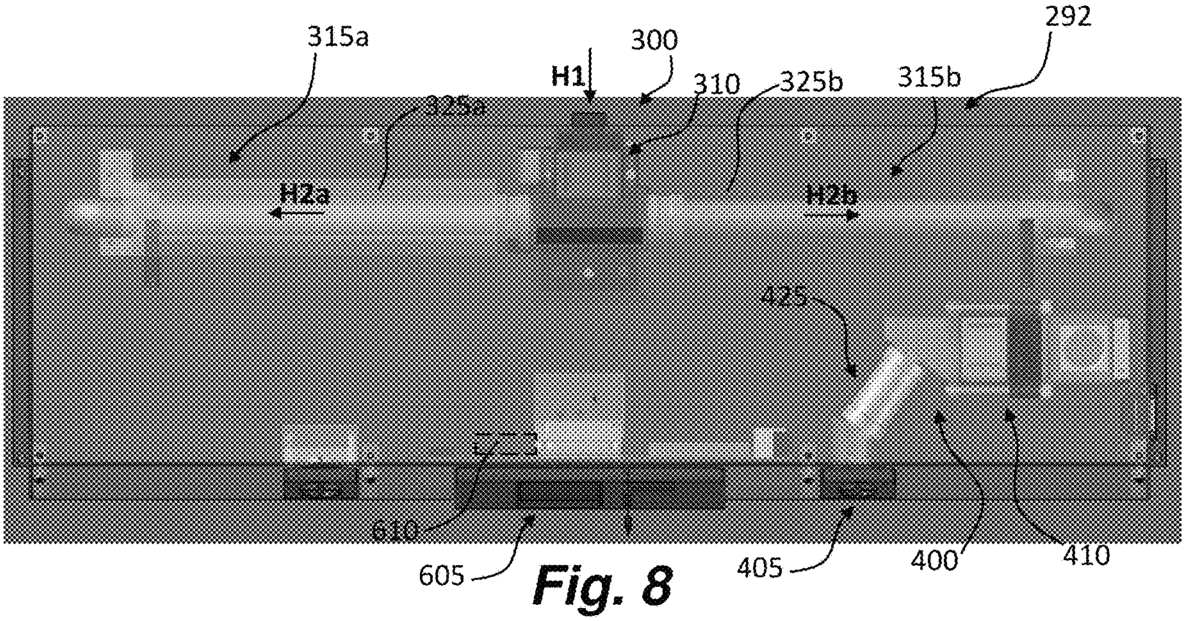
FIG. 8 is a top view of the exemplary embodiment of the present invention illustrated in FIG. 6.

In at least some exemplary embodiments and as illustrated in FIGS. 6 to 8, at least some of the exemplary disclosed components of incubator 105 may be supported by a module housing 292 of structural and insulation system 200. Module housing 292 may be formed from similar materials as components of structural and insulation system 200 for example as described above. Module housing 292 may be received and disposed within an upper or top portion of insulated housing 205.

As illustrated in FIGS. 1 and 2, structural and insulation system 200 may also include one or more carrying accessories 295 that may be attached to an exterior surface of insulated housing 205. In at least some exemplary embodiments, carrying accessory 295 may include a carrying strap loop (e.g., tough carrying strap loop) that may be attached (e.g., via any suitable mechanical fasteners) to an exterior surface portion of incubator 105. Carrying accessory 295 may be formed from any suitable material such as, for example, fabric, flexible plastic, and/or any other suitable material. For example, carrying accessories 295 may be attached at four corner areas of a lower or bottom portion of incubator 105. Carrying accessories 295 may facilitate transport of incubator 105 and/or securing of incubator 105 to a table during use and/or to a transportation surface (e.g., a truck bed).

Incubation system 100 may have separate heating and ventilation systems. For example, heating system 300 and ventilation system 400 may be separate from each other as illustrated in FIGS. 2, 4, 5, 7, and 8. For example, heating system 300 and ventilation system 400 may not be fluidly connected, so that heating airflow in heating system 300 is separate from and not fluidly connected to ventilation airflow in ventilation system 400 (e.g., other than both airflows being drawn from and exhausted into incubation chamber 235). The air supply system provided by ventilation system 400 may thereby be separate from heating system 300 (e.g., other than both airflows being drawn from and exhausted into incubation chamber 235), thereby simplifying maintenance of incubation system 100. For example as illustrated in FIGS. 2, 4, 5, 7, and 8 and described further below, the exemplary disclosed heating airflow of heating system 300 may utilize recirculating airflow (e.g., based on being fluidly separate from and disconnected from the exemplary disclosed ventilation airflow of ventilation system 400), which may save energy and decrease an amount of energy used by incubation system 100.

As illustrated in FIGS. 2, 4, 5, 7, and 8, heating system 300 may include a heat intake passage 305, a heat circulation fan 310, a plurality of heat exhaust passages 315*a* and 315*b*, and a plurality of heat exhaust nozzles 320*a* and 320*b*, which may together form a plurality of recirculating heating airflow passages that transfer recirculating heating airflow H1, H2*a*, H3*a*, H2*b*, and H3*b*. Heat intake passage 305 may transfer heating airflow H1 to heat circulation fan 310, where the heating airflow may split into heating airflow H2*a* and H2*b*. Heat exhaust passage 315*a* may transfer heating airflow H2*a* to heat exhaust nozzle 320*a*, where it may be transferred via heat exhaust nozzle 320*a* into incubation chamber 235. Similarly, heat exhaust passage 315*b* may transfer heating airflow H2*b* to heat exhaust nozzle 320*b*, where it may be transferred via heat exhaust nozzle 320*b* into incubation chamber 235. Heat intake passage 305 may then draw air from incubation chamber 235 based on operation of heat circulation fan 310, thereby facilitating continuous recirculation of heating airflow. Heating airflow H1, H2*a*, H3*a*, H2*b*, and H3*b* may not be fluidly connected to the exemplary disclosed ventilation airflow described below (e.g., other than both airflows being drawn from and exhausted into incubation chamber 235).

Heat circulation fan 310 may be any suitable component for pressurizing an airflow to draw heating airflow H1 from incubation chamber 235 and transferring the airflow as heating airflow H2*a*, H2*b*, H3*a*, and H3*b* via respective heat exhaust passages 315*a* and 315*b* (e.g., where the flowing air may be heated as described below) and heat exhaust nozzles 320*a* and 320*b* to be transferred back into incubation chamber 235. Heat circulation fan 310 may be an axial fan such as a propeller fan or a centrifugal blower design.

Figure 15:
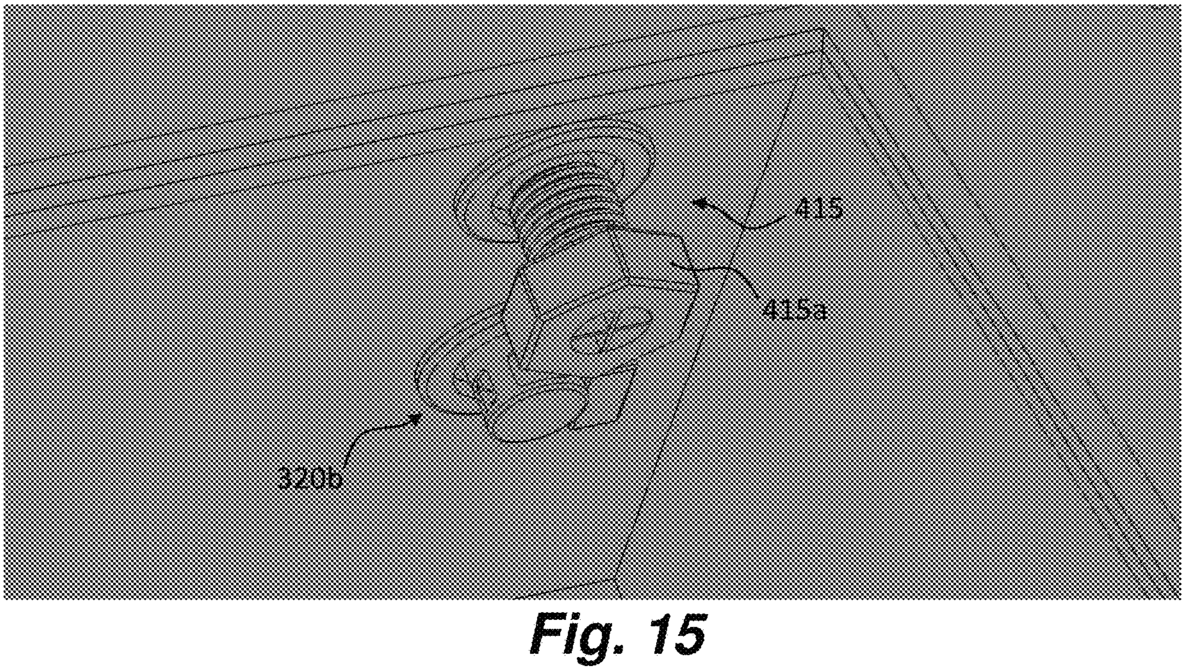
FIG. 15 is a detailed, perspective view of an exemplary embodiment of the present invention.
Figure 16:
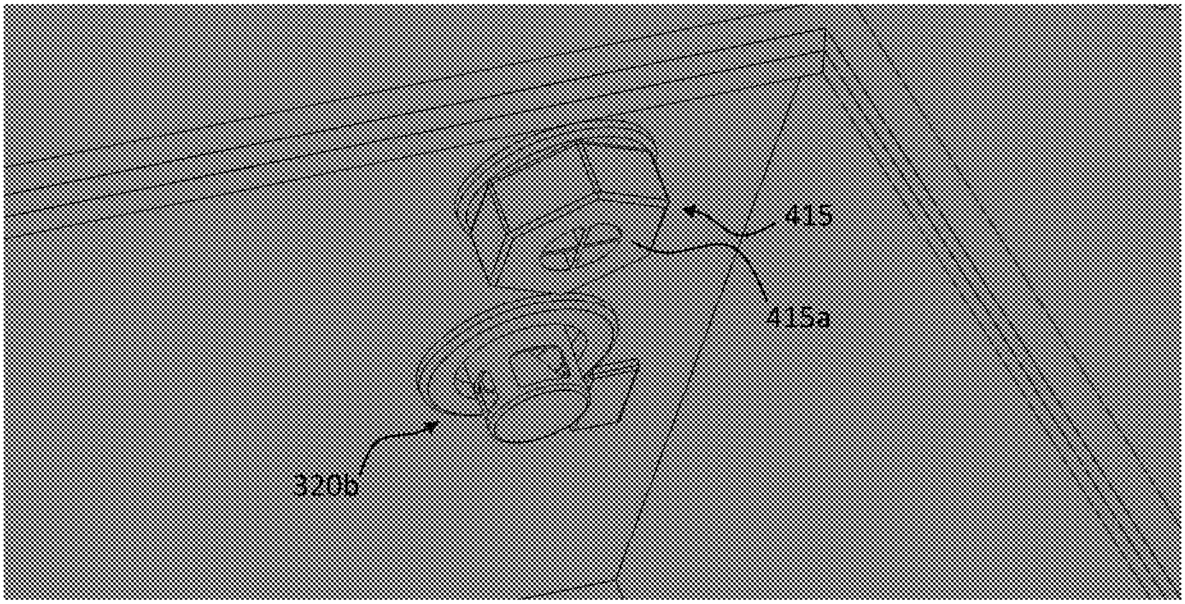
FIG. 16 is another detailed, perspective view of the exemplary embodiment of the present invention illustrated in FIG. 15.

Heat exhaust nozzles 320*a* and 320*b* may be any suitable components for exhausting airflow H3*a* and H3*b* into incubation chamber 235. Heat exhaust nozzles 320*a* and 320*b* may be any suitable nozzles for axial airflow. Heat exhaust nozzles 320*a* and 320*b* may be round jet nozzles, cluster nozzles, flat jet nozzles, or any other suitable type of nozzles. For example, heat exhaust nozzles 320*a* and 320*b* may be any suitable type of nozzles that may quietly and with low restriction serve to optimize the homogeneity of the temperature within the infant chamber. FIGS. 15 and 16 illustrate a detailed view of heat exhaust nozzle 320*b* (e.g., heat exhaust nozzle 320*a* may be similar).

Heat intake passage 305 and heat exhaust passages 315*a* and 315*b* may be formed from any suitable member or members for transferring airflow such as, for example, pipes or shafts. The exemplary disclosed passages may be formed from similar material as exterior housing assembly 210. The exemplary disclosed passages may include any suitable components for varying a path (e.g., a direction) of airflow such as, for example, elbows or other suitable fittings. In at least some exemplary embodiments, the exemplary disclosed heat air intake entrance (e.g., of heat intake passage 305) may have a fine mesh mosquito screen to substantially prevent bugs from laying eggs in that system and to block liquids (e.g., of any origin including the infant) from entering the heat air intake entrance.

A heating component 325*a* may be disposed at and/or attached to heat exhaust passage 315*a*, and a heating component 325*b* may be disposed at and/or attached to heat exhaust passage 315*b*. In at least some exemplary embodiments, one of heating components 325*a* and 325*b* may be included and the other of heating components 325*a* and 325*b* may be omitted (e.g., a single heating component may be included). Heating components 325*a* and 325*b* may be disposed upstream of incubation chamber 235 and configured to heat heating air flow being returned to incubation chamber 235. Heating components 325*a* and 325*b* may be any suitable heating component for heating airflow H2*a* and H2*b*. For example, heating components 325*a* and 325*b* may include any suitable conductive elements such as, for example, metal heating elements, ceramic heating elements, thick film heating elements, semiconductor heating elements, polymeric heating elements, and/or any other suitable heating elements. In at least some exemplary embodiments, heating components 325*a* and 325*b* may include metal wiring such as copper wiring or coils (e.g., or any other suitable wiring) that may be wrapped or wound around respective heat exhaust passages 315*a* and 315*b* (e.g., around an exterior surface of heat exhaust passages 315*a* and 315*b*). Heating components 325*a* and 325*b* may be heated via any suitable technique such as, for example, electrical heating (e.g., via resistive heating and/or any other suitable heating technique).

In at least some exemplary embodiments, heating system 300 may include dual (e.g., redundant) heater pipes (e.g., heat exhaust passages 315*a* and 315*b* heated by respective heating components 325*a* and 325*b*) with a heat circulation fan (e.g., heat circulation fan 310). Also for example as described above, a single exemplary disclosed heating component disposed at one of the exemplary disclosed heat exhaust passages may be used. Heat exhaust passages 315*a* and 315*b* may recirculate heated air directly into incubation chamber 235 via respective heat exhaust nozzles 320*a* and 320*b*. As the exemplary disclosed air circuit may have intake components that may contain pathogens (e.g., based on an environment in which incubation system 100 may be used), a last or final part of the air circuit (e.g., heat exhaust passages 315*a* and 315*b* heated by respective heating components 325*a* and/or 325*b*) may be heated to sterilize heating airflow H2*a* and H2*b* to substantially eliminate (e.g., kill) these pathogens. For example, heating airflow H2*a* and H2*b* may be heated to any suitable temperature for sterilizing air such as, for example, up to about 90° C. (e.g., hot enough to sterilize, but not hot enough to start a fire and/or cause flammability in the heating airflow). Accordingly, incubation system 100 may maintain a flammability category of V0 (e.g., have V0 fire resistance). The chamber air intake at an intake of heat intake passage 305 may be protected with a screen (e.g., a stainless steel mosquito screen or a screen of any other suitable material) to substantially prevent bugs, which may enter incubation chamber 235 when door assembly 255 and/or access doors 280 are open, from nesting in incubator 105.

As illustrated in FIGS. 1-8, 15, and 16, ventilation system 400 may include a ventilation air intake 405, a ventilation fan 410, a ceiling filter 415, and one or more ventilation exhaust vents 420 that may form a plurality of ventilation airflow passages configured to draw ventilation airflow (e.g., fresh air) from outside of incubator 105 and into incubation chamber 235, and vent out ventilation airflow from incubation chamber 235. Ventilation fan 410 may operate to draw fresh air through air intake 405 and into incubation chamber 235 via ceiling filter 415 (e.g., illustrated in FIGS. 15 and

16). Air may simultaneously be vented out of incubation chamber 235 via one or more ventilation exhaust vents 420 to complete a ventilation airflow of incubation system 100. A ventilation passage 425, which may be generally similar to heat intake passage 305, may fluidly connect air intake 405, ventilation fan 410, and ceiling filter 415.

As illustrated in FIGS. 1-8, ventilation air intake 405 may be a chamber air intake that may have any suitable screen (e.g., a stainless steel mosquito screen or a screen of any other suitable material). For example, ventilation air intake 405 may be and/or include a screen that may serve as a mosquito screen. Ventilation air intake 405 may operate to screen intake air drawn into incubator 105 from the ambient air surrounding incubator 105. Ventilation air intake 405 may include any suitable mass flow sensor that may emit an alarm if ventilation airflow through ventilation system 400 is blocked. The mass flow sensor may be a vane air flow meter or any other suitable type of air flow meter. For example, ventilation air intake 405 may be an assembly that may include a screen and/or mass flow sensor that may serve as both a mosquito screen and mass flow sensor.

As illustrated in FIGS. 2, 4, 5, 7, and 8, ventilation fan 410 may be any suitable component for pressurizing an airflow to draw fresh air through ventilation air intake 405 and into incubation chamber 235 via ceiling filter 415. Ventilation fan 410 may be generally similar to heat circulation fan 310. Ventilation fan 410 may include a screen similar to ventilation air intake 405.

Ceiling filter 415 may be fluidly connected with ventilation passage 425 and may filter air passing from ventilation passage 425 into incubation chamber 235. As illustrated in FIGS. 15 and 16, ceiling filter 415 may be an exhaust assembly including a replaceable screw-in filter 415*a*. For example, replaceable screw-in filter 415*a* may be disposed in the exemplary disclosed plurality of ventilation airflow passages upstream of incubation chamber 235 and configured to filter the ventilation airflow entering incubation chamber 235. Screw-in filter 415*a* may be a relatively easily replaceable filter that may be removed and replaced with a new (e.g., or cleaned) screw-in filter 415*a*. For example, ceiling filter 415 may be an inexpensive (e.g., a very inexpensive), replaceable screw-in filter that may substantially block TB bacteria and/or mold spores. For example, screw-in filter 415*a* may be easily removed, cleaned, and/or replaced by end users of incubation system 100. In at least some exemplary embodiments, ceiling filter 415 may be a plastic and/or metal filter (e.g., or any other suitable filter) for filtering air.

As illustrated in FIGS. 1-5, one or more ventilation exhaust vents 420 may be disposed in one or more door members 270. Ventilation exhaust vent 420 may be any suitable vent for exhausting air out of incubation chamber 235 to complete a ventilation air flow of incubation system 100. Ventilation exhaust vent 420 may be formed from materials and include components generally similar to the exemplary disclosed stainless steel screen mosquito filter. Ventilation exhaust vent 420 may be disposed at a relatively low position on door assembly 255 (e.g., at a lower half portion or third portion of door assembly 255), which may facilitate exhaust of $CO_2$, which may be generally disposed relatively lower in incubator 105 based on $CO_2$ being relatively heavier than $O_2$.

In at least some exemplary embodiments, ventilation system 400 may include a separate ventilation intake fan (e.g., ventilation fan 410) from a fan (e.g., heat circulation fan 310) of heating system 300. Ventilation fan 410 may transport air from outside of incubator 105 into incubation chamber 235 to maintain suitable (e.g., proper or healthy $O_2$ and $CO_2$) levels in incubation chamber 235. Ventilation system 400 may operate to maintain incubation chamber 235 at a positive pressure (e.g., slightly positive pressure relative to ambient air surrounding incubator 105) for example when an exemplary disclosed door is open to incubation chamber 235. For example, a gentle continuous positive pressure provided by ventilation system 400 may substantially prevent and/or reduce a likelihood that air from any other part of incubator 105, which may eventually contain pathogens, will enter incubation chamber 235.

Figure 14:
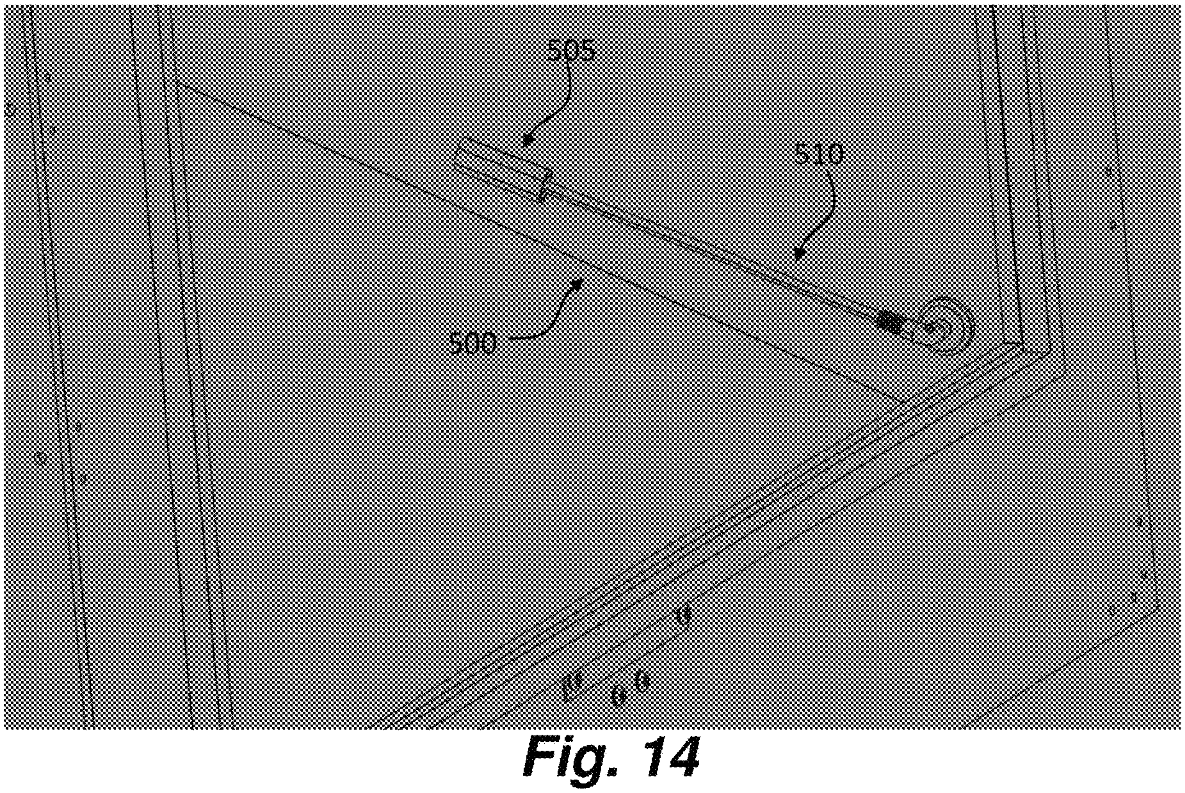
FIG. 14 is a detailed, perspective view of an exemplary embodiment of the present invention.
Figure 14A:
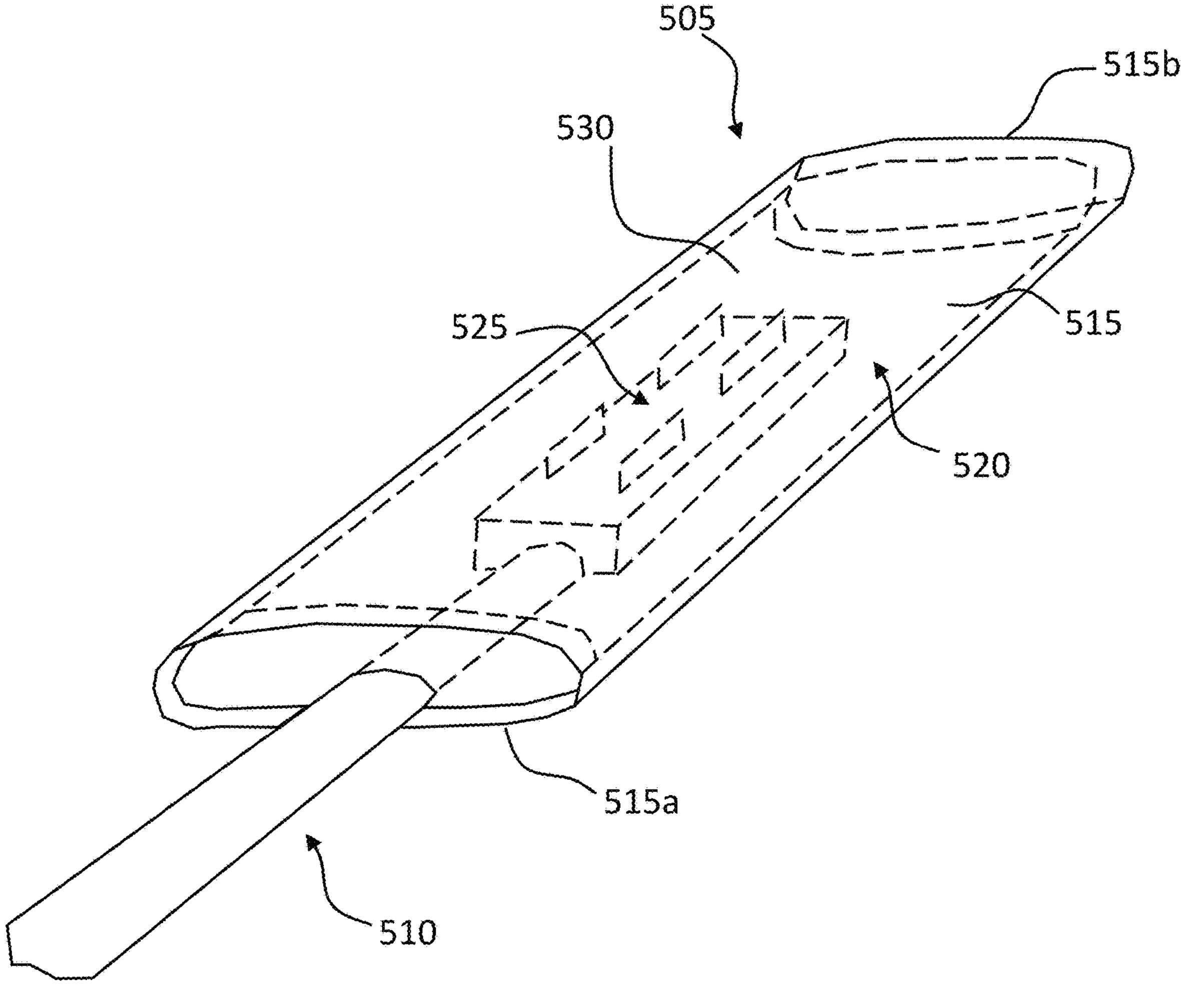
FIG. 14A is a detailed, perspective view of an exemplary embodiment of the present invention.

As illustrated in FIGS. 14 and 14A, skin sensor system 500 may include a skin sensor 505 that may be connected to control system 600 and power system 700 via a skin sensor connection assembly 510. Skin sensor connection assembly 510 may include electrical lines for providing electrical connection and transfer of signals and/or data between skin sensor 505 and control system 600 and power system 700 for powering and controlling an operation of skin sensor 505. Skin sensor connection assembly 510 may be attached (e.g., removably attached via any suitable technique such as removably attachable mechanical and/or electrical connection) to structural and insulation system 200 (e.g., a wall of insulated housing 205 forming incubation chamber 235) and may be connected to skin sensor 505 that may be disposed in incubation chamber 235.

Skin sensor 505 may sense a skin temperature of an infant being cared for in incubation chamber 235. For example, skin sensor 505 may be placed under an arm (e.g., at an armpit) or under a belly of an infant being incubated using incubator 105.

As illustrated in FIG. 14A, skin sensor 505 may include a sensor housing 515. Sensor housing may be formed from any suitable structural material such as, for example, metal or plastic material. In at least some exemplary embodiments, sensor housing 515 may be formed from steel (e.g., stainless steel), or any other suitable biocompatible, thermally conductive material. Sensor housing 515 may be open at one or both sensor ends 515*a* and 515*a*. For example, sensor housing 515 may form a sensor cavity 520 that may be open at both ends 515*a* and 515*b*. A sensor circuit board 525 may be disposed in sensor cavity 520. Sensor circuit board 525 may include similar components (e.g., including hardware and/or software) as described below regarding control system 600, and may control an operation of skin sensor 505. Sensor circuit board 525 may include a thermocouple sensor, a resistance-temperature detector, a negative temperature coefficient thermistor, an infrared sensor, a "smart" semiconductor sensor, a silicon diode sensor, and/or any other suitable thermal sensor.

Sensor circuit board 525 may be disposed in a fill material 530 that may be disposed in sensor cavity 520. For example, fill material 530 may substantially entirely surround sensor circuit board 525 so that sensor circuit board 525 is encapsulated in fill material 530 (e.g., and a portion of skin sensor connection assembly 510 extending into sensor cavity 520 to connect to sensor circuit board 525 may also be encapsulated in fill material 530). Fill material 530 may be any suitable material having relatively good (e.g., high) thermal conductivity and/or any suitable material for structurally supporting and protecting sensor circuit board 525 within sensor cavity 520. For example, fill material 530 may be any suitable resin material such as epoxy material, acrylic material, polyurethane material, and/or any other suitable material for surrounding and/or encapsulating sensor circuit board 525 within sensor cavity 520.

In at least some exemplary embodiments, skin sensor 505 may be formed based on inserting sensor circuit board 525 connected to an end portion of skin sensor connection assembly 510 into an open sensor end 515*a* or 515*b* or sensor housing 515. As sensor circuit board 525 is held in a middle portion of sensor cavity 520, away from walls of sensor housing 515 (e.g., so that sensor circuit board 525 is held in a middle or central portion of sensor cavity 520), sensor cavity 520 may be substantially filled with fill material 530 so that sensor circuit board 525 is surrounded by and substantially encapsulated in fill material 530 filling sensor cavity 520 (e.g., fill material 530 may for example be in an uncured and/or fluid state as it fills sensor cavity 520). Sensor circuit board 525 may continue to be held, supported, and/or maintained in a middle portion of sensor cavity 520, away from walls of sensor housing 515 (e.g., so that sensor circuit board 525 is held in a middle portion of sensor cavity 520) until fill material 530 has cured into a substantially solid state.

For example based on the exemplary disclosed configuration described above, skin sensor 505 may be relatively easily cleaned. For example, skin sensor 505 may be cleaned based on being boiled in water or any other suitable sterilizing technique. For example, fill material 530 in the exemplary disclosed cured state may protect, surround, and/or encapsulate sensor circuit board 525, thereby substantially protecting sensor circuit board 525 from being damaged and/or negatively affected by temperatures and contact associated with the exemplary disclosed cleaning methods (e.g., boiling water), because fill material 530 and sensor housing 515 may substantially shield and protect sensor circuit board 525 from contact during cleaning (e.g., during boiling in water to kill any pathogens on or at skin sensor 505). In at least some exemplary embodiments, some or substantially all of skin sensor connection assembly 510 and skin sensor 505 may be detached and removed from incubator 105 so that skin sensor 505 may be cleaned. Skin sensor 505 may thereby provide a non-disposable and relatively easily sterilizable skin sensor for incubation system 100. An operation of skin sensor 505 may thereby avoid the relatively expensive use of disposable sensors.

As illustrated in FIGS. 1 to 8, control system 600 may include a user interface 605. User interface 605 may be any suitable user interface for receiving input and/or providing output (e.g., text data, image data, and/or audio data) to a user. User interface 605 may be, for example, a touchscreen device. For example, user interface 605 may include a display (e.g., a computing device display, a touchscreen display, and/or any other suitable type of display) that may provide output, image data, and/or any other desired output or input prompt to a user. For example, the exemplary disclosed display may include a graphical user interface to facilitate entry of input by a user and/or receiving output such as image data, text data, and/or audio data (e.g., an alarm, instructions, and/or similar output). For example, user interface 605 may emit alarms and/or output from the exemplary disclosed sensors described above. User interface 605 may include input components such as buttons and dials, a tactile-based device for entering input and receiving output based on touch or feel, and/or any other suitable interface component.

In at least some exemplary embodiments, user interface 605 may be a touch screen such as, for example, a relatively small color touch screen that may provide instructions and diagnostics displays to a user. For example, user interface 605 may be a resistive touch screen that may substantially avoid issues that a capacitive touch screen may have when a user's hands are wet.

Control system 600 may include a controller 610. Controller 610 may be integrated with user interface 605 or may be a separate component configured to communicate (e.g., receive and transmit data and/or signals) with user interface 605. Controller 610 may control an operation of incubation system 100 for example as described herein. Controller 610 may be any suitable computing device for controlling an operation of components of incubation system 100. Controller 610 may include for example a processor (e.g., micro-processing logic control device) and/or board components. Controller 610 may include data storage. For example, controller 610 may have storage for storing programming instructions. Controller 610 may communicate with other components (e.g., the exemplary disclosed components of heating system 300, ventilation system 400, skin sensor system 500, and/or power system 700) of incubation system 100 via wire (e.g., direct wire communication), wireless, a LAN (e.g., via Ethernet LAN), a WAN, a WiFi network, Bluetooth, ZigBee, NFC, IrDA, and/or any other suitable communication technique. A user may control controller 610 (e.g., provide input and/or commands) via user interface 605, a user device (e.g., a smart device such as a smart phone or tablet), and/or any other suitable communication and/or control technique.

Electrical connectors may connect the exemplary disclosed components of heating system 300, ventilation system 400, skin sensor system 500, control system 600 and power system 700. The electrical connectors may be any suitable connector for transferring electrical energy, signals, and/or data such as, for example, electrical wires, lines, or cords.

Figure 13:
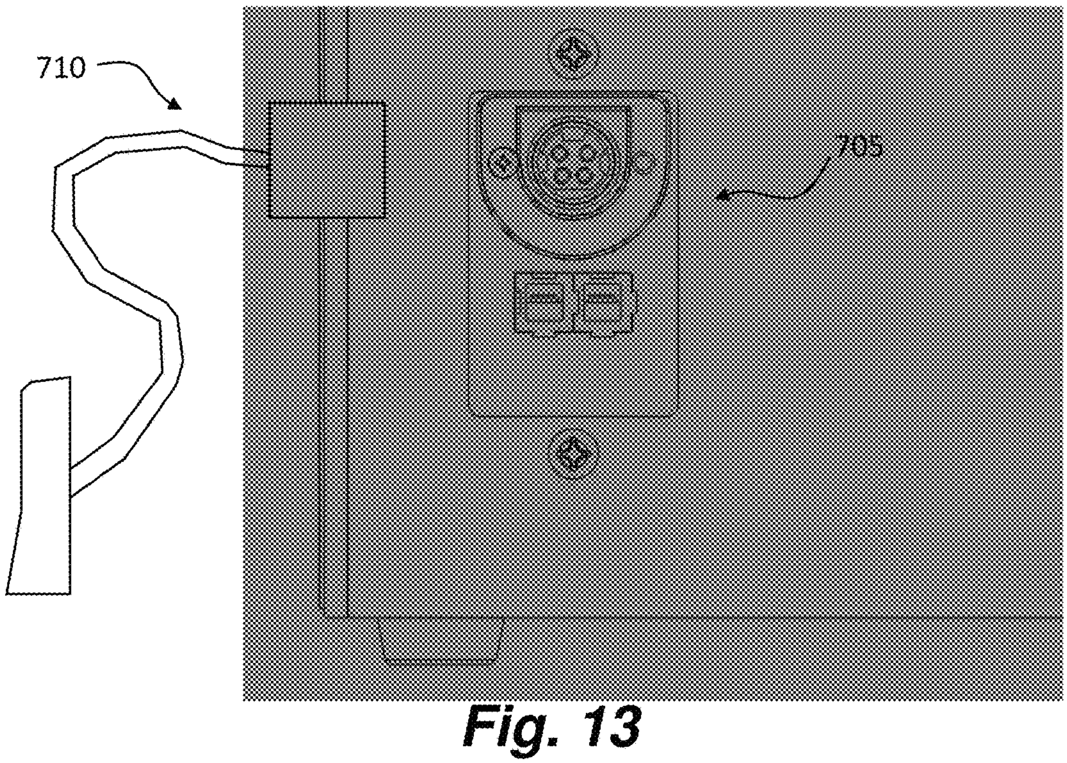
FIG. 13 is a detailed, perspective view of an exemplary embodiment of the present invention.

As illustrated in FIG. 13, power system 700 may include a power connector 705 and a power supply 710. Power supply 710 may be any suitable power supply for transforming AC power (e.g., from a wall outlet or other AC power source) to DC power to power incubator 105. For example, power supply 710 may be electrically connected between a wall outlet or other AC power supply (e.g., or DC power supply) and power connector 705 that may be integrated into structural and insulation system 200 (e.g., into a wall of insulated housing 205). Power connector 705 may include an electrical connector for receiving a plug or similar electrical connector of power supply 710. Power connector 705 may be electrically connected (e.g., via the exemplary disclosed electrical connectors) to the exemplary disclosed components of heating system 300, ventilation system 400, skin sensor system 500, control system 600 and power system 700, so that these exemplary disclosed components may be supplied power via power system 700.

Power supply 710 may include any suitable power storage for storing energy (e.g., electrical energy) and providing stored energy to power incubator 105. Power supply 710 may include a battery such as, for example, a nickel-metal hydride battery, a lithium-iron battery, an ultracapacitor battery, a lead-acid battery, a nickel cadmium battery, or any other suitable type of battery. In at least some exemplary embodiments, power supply 710 may include an ultracapacitor that may provide sufficient energy to power the exemplary disclosed alarms (e.g., last ditch LED and/or audible alarms) to alert caretakers when incubator 105 loses all power. In at least some exemplary embodiments, power supply 710 may include and/or be configured to be electrically connected to an external battery backup (e.g., any suitable lead-acid battery such as a 12V lead-acid battery).

For example, power supply 710 may be electrically connected to a car battery or other similar battery when outlet power (e.g., grid power) is not available. An input of power supply 710 may be protected against reverse polarity and/or improper voltage. A battery of power supply 710 may be charged (e.g., trickle-charged) when AC power is present and being provided to power supply 710. Power supply 710 may be charged via being connected to a wall outlet (e.g., via an extension cord if applicable). Power supply 710 may also be charged via a portable power supply and/or generator. In at least some exemplary embodiments, power supply 710 may be an external, medical-grade, low voltage DC power supply that may be adaptable to poorly regulated AC voltage and/or may protect an infant being incubated and/or operators against improperly grounded outlets.

In at least some exemplary embodiments, incubation system 100 may be formed to facilitate manufacturing at a relatively low price (e.g., based on the exemplary disclosed configurations described above). For example, incubation system 100 may be produced at about 1/10th the price of a relatively inexpensive developed-world hospital unit. For example, some or most of the exemplary disclosed components may be 3D printed parts, without use (e.g., or with relatively little use) of injection molding, sheet metal, castings, and/or similar relatively expensive techniques.

The exemplary disclosed system, apparatus, and method may be used in any suitable application for infant incubation. The exemplary disclosed system, apparatus, and method may be used in any suitable application for providing infant incubation in facilities outside of functioning hospitals. For example, the exemplary disclosed system, apparatus, and method may be used in any suitable application for providing infant incubation in facilities or areas having unreliable electrical power access and/or relatively poor sanitary conditions such as, for example, areas of the developing world, areas that have undergone natural disasters, remote areas, and/or any other area having significant environmental and/or infrastructure challenges. For example, incubator 105 may maintain up to a 26° C. differential with ambient air outside of incubator 105 based on operation at 100 W (e.g., to provide heat on cold nights in a facility lacking glass in windows and/or effective insulation). Also in at least some exemplary embodiments, incubation chamber 235 may include lighting (e.g., diffused white LED lighting) having an intensity controlled via control system 600.

Figure 17:
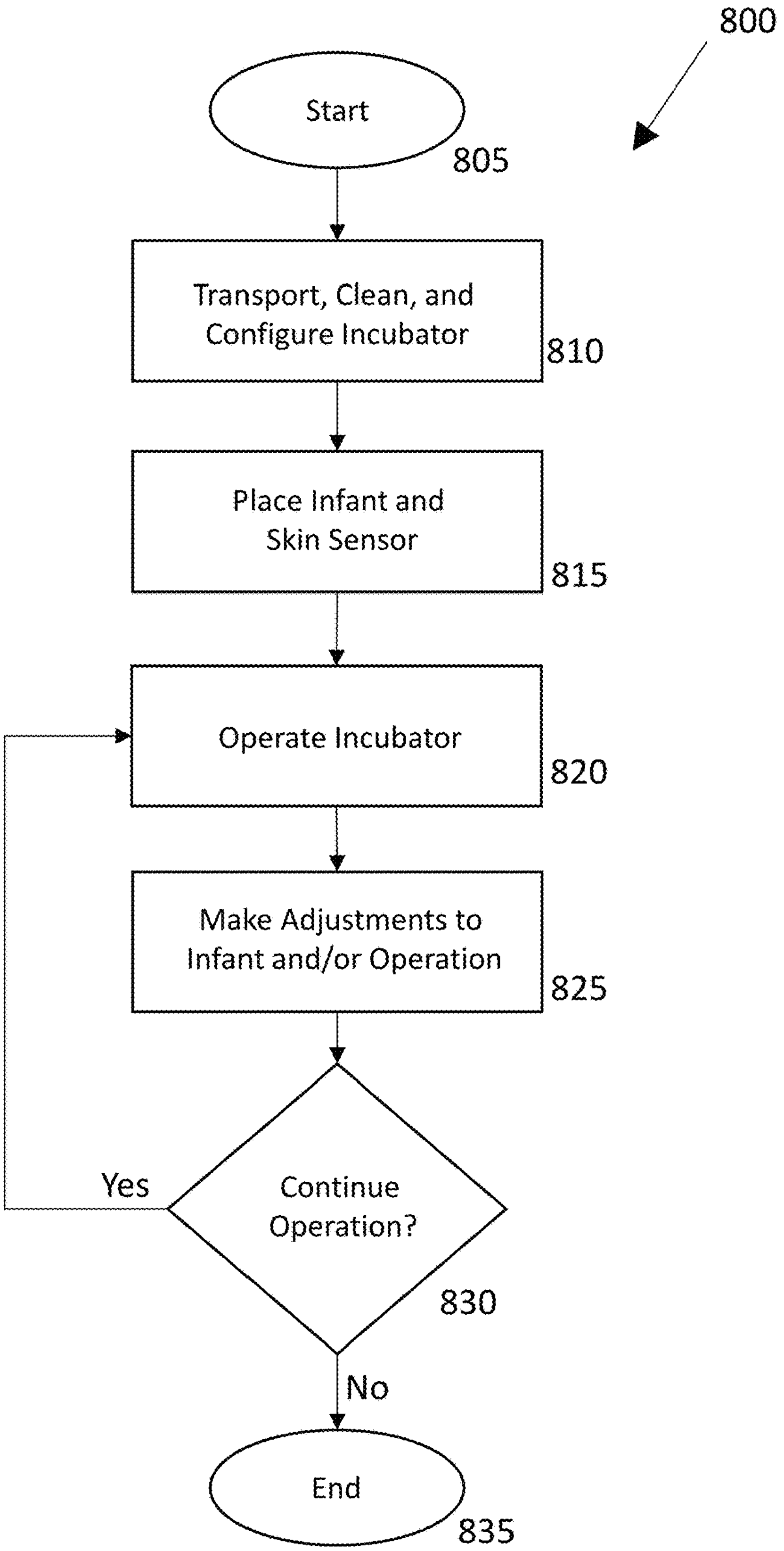
FIG. 17 illustrates an exemplary process of using at least some exemplary embodiments of the present disclosure.

FIG. 17 illustrates an exemplary process of using the exemplary disclosed system and apparatus. Process 800 begins at step 805. At step 810, incubation system 100 may be transported, cleaned, and configured. For example, carrying accessories 295 may facilitate transport of incubator 105 and/or securing of incubator 105 during use as described above. Incubator 105 may be cleaned, including for example cleaning exposed surfaces of insulated housing, surfaces of incubation chamber 235 and components of skin sensor system 500, and/or surfaces of door assembly 255 and access doors 280. For example as described above, skin sensor 505 may be cleaned based on being boiled in water or any other suitable sterilizing technique. Screw-in filter 415*a* may be removed, cleaned and replaced (e.g., or removed and replaced with a new or relatively easily replaceable filter that may be removed and replaced with a new screw-in filter 415*a*) for example as described above. Incubation system 100 may be configured for example as described above, including configuring power connector 705 and power supply 710 as described above. Power may thereby be provided to incubator 105.

At step 815, an infant to be cared for (e.g., incubated) may be placed in incubator 105. For example, the exemplary disclosed door of door assembly 255 may be opened and the infant may be placed in incubation chamber 235. Magnetic catch assemblies 255*a* may facilitate a one-hand operation of door assembly 255 for example as described above. Skin sensor 505 may be placed on the infant as described above. Door assembly 255 may be closed. Incubator 105 may already be operating as described at step 820 below when the infant is placed in incubation chamber 235.

At step 820, incubation system 100 may operate to incubate the infant in incubator 105. Because heating system 300 and ventilation system 400 may not be fluidly connected, heating airflow in heating system 300 may be provided separately from ventilation airflow in ventilation system 400 as described above. As described above, heat intake passage 305 may transfer heating airflow H1 to heat circulation fan 310, where the heating airflow may split into heating airflow H2*a* and H2*b*. Heat exhaust passage 315*a* may transfer heating airflow H2*a* to heat exhaust nozzle 320*a*, where it may be transferred via heat exhaust nozzle 320*a* into incubation chamber 235, and heat exhaust passage 315*b* may transfer heating airflow H2*b* to heat exhaust nozzle 320*b*, where it may be transferred via heat exhaust nozzle 320*b* into incubation chamber 235. Heat intake passage 305 may then draw air from incubation chamber 235 based on operation of heat circulation fan 310, facilitating continuous recirculation of heating airflow. A separate ventilation airflow may also be provided, with ventilation fan 410 operating to draw fresh air through ventilation air intake 405 and into incubation chamber 235 via ceiling filter 415 as described above. Air may simultaneously be vented out of incubation chamber 235 via one or more ventilation exhaust vents 420, thereby completing a ventilation airflow of incubation system 100 (e.g., that may be separate from the exemplary disclosed heating airflow). As heating system 300 and ventilation system 400 operate, skin sensor 505 may sense a skin temperature of an infant being cared for in incubation chamber 235, with data and/or signals indicative of the skin temperature being transferred to control system 600. Control system 600 may control an operation of heating system 300, ventilation system 400, and skin sensor system 500. Power system 700 may provide power to heating system 300, ventilation system 400, skin sensor system 500, and control system 600.

Control system 600 may provide output, alarms, and/or notifications to users of incubation system 100 via user interface 605 and/or any other suitable components of incubation system 100. For example, control system 600 may provide output, alarms, and/or notifications of a skin temperature of an infant being cared for in incubation chamber 235 based on data and/or signals provided to control system 600 via skin sensor system 500 (e.g., output, alarms, and/or notifications of a skin temperature that is lower than a threshold low healthy temperature and/or higher than a threshold high healthy temperature). Similarly, control system 600 may provide output, alarms, and/or notifications of door assembly 255 (e.g., and/or access door 280) not being properly closed based on data or signals provided by magnetic sensor 290 for example as described above. Similarly, control system 600 may provide output, alarms, and/or notifications of ventilation airflow being blocked based on data or signals provided by the exemplary disclosed mass flow sensor of ventilation air intake 405 for example as described above. Users may adjust and/or control an operation of heating system 300, ventilation system 400, skin sensor system 500, and power system 700 by providing input to user interface 605 (e.g., and/or any suitable user device that may communicate with controller 610).

At step 825, caregivers may make adjustments to care being given to an infant being incubated and/or operation of incubation system 100. For example, one or more access doors 280 may be opened to access incubation chamber 235 as described above. Skin sensor 505 placed on the infant may be adjusted. Any other suitable adjustments may be made to the infant and/or any other items disposed in incubation chamber 235. Access doors 280 may be closed and sealed after desired adjustments are made. Any desired adjustment may be made to incubator 105 via user interface 605 (e.g., and/or any suitable user device that may communicate with controller 610).

At step 830 it may be determined whether operation of incubation system 100 is to be continued. If use is to be continued, process 800 returns to step 820. As many iterations as desired of steps 820 through 830 may be performed. If use is not to be continued, process 800 ends at step 835.

The invention includes other illustrative embodiments ("Embodiments") as follows.

Embodiment 1: An incubator, comprising: an insulated housing that forms an incubation chamber; a plurality of recirculating heating airflow passages configured to draw a heating airflow from the incubation chamber, heat the heating airflow, and return the heating airflow to the incubation chamber; and a plurality of ventilation airflow passages configured to draw a ventilation airflow from outside of the incubator and into the incubation chamber, and vent the ventilation airflow out of the incubation chamber; wherein the plurality of recirculating heating airflow passages are separate from the plurality of ventilation airflow passages.

Embodiment 2: The incubator of Embodiment 1, further comprising metal wiring wrapped around a heat exhaust passage of the plurality of recirculating heating airflow passages disposed upstream of the incubation chamber and configured to heat the heating airflow returning to the incubation chamber.

Embodiment 3: The incubator of Embodiment 1, further comprising a replaceable screw-in air filter disposed in the plurality of ventilation airflow passages upstream of the incubation chamber and configured to filter the ventilation airflow entering the incubation chamber.

Embodiment 4: The incubator of Embodiment 1, further comprising a mosquito screen of a ventilation air intake of the plurality of ventilation airflow passages configured to draw the ventilation airflow from outside of the incubator.

Embodiment 5: The incubator of Embodiment 1, further comprising a mass flow sensor integrated into a ventilation air intake of the plurality of ventilation airflow passages configured to draw the ventilation airflow from outside of the incubator.

Embodiment 6: The incubator of Embodiment 1, further comprising a heating fan of the plurality of recirculating heating airflow passages, and a ventilation fan of the plurality of ventilation airflow passages.

Embodiment 7: The incubator of Embodiment 6, further comprising a touchscreen configured to receive input for a controller that controls the heating fan of the plurality of recirculating heating airflow passages and the ventilation fan of the plurality of ventilation airflow passages.

Embodiment 8: The incubator of Embodiment 1, wherein the touchscreen, the controller, the heating fan, and the ventilation fan are configured to be powered by a wall outlet or a 12V lead-acid battery.

Embodiment 9: An incubator, comprising: an exterior housing assembly; an interior housing assembly; and an insulation layer disposed between the exterior housing assembly and the interior housing assembly; wherein the interior housing assembly, the insulation layer, and the exterior housing assembly form an insulated housing that forms an incubation chamber; and wherein the exterior housing assembly and the interior housing assembly are formed from a plastic material.

Embodiment 10: The incubator of Embodiment 9, wherein the insulation layer is formed from foam material.

Embodiment 11: The incubator of Embodiment 9, wherein the insulation layer is formed from at least one selected from the group of closed cell foam, foam cell material, polyethylene foam, polyurethane foam, neoprene foam, latex foam, gel foam, and combinations thereof.

Embodiment 12: The incubator of Embodiment 9, wherein the insulation layer is formed from at least one selected from the group of foam, mineral wool, perlite, polyurethane, polystyrene, cellulose, fiber material, air, and combinations thereof.

Embodiment 13: The incubator of Embodiment 9, wherein the exterior housing assembly and the interior housing assembly are formed from at least one selected from the group of HDPE, polyvinyl chloride material, acrylonitrile butadiene styrene material, polycarbonate material, PPS material, Polypropylene, and combinations thereof.

Embodiment 14: The incubator of Embodiment 9, further comprising a door assembly rotatably attached to the insulated housing and including a first door member and a second door member separated from each other by an air gap.

Embodiment 15: The incubator of Embodiment 14, further comprising one or more access doors configured to open and close at apertures of the door assembly.

Embodiment 16: The incubator of Embodiment 14, further comprising at least one of a magnetic catch assembly, a magnetic sensor, and a memory foam seal disposed at the door assembly.

Embodiment 17: The incubator of Embodiment 9, further comprising carrying straps disposed at an exterior surface of the exterior housing, which faces away from the insulation layer.

Embodiment 18: An incubator, comprising: an insulated housing that forms an incubation chamber; and a skin sensor disposed in the incubation chamber, the skin sensor including a sensor housing, a sensor circuit board disposed in the sensor housing, and a fill material encapsulating the sensor circuit board and disposed between the sensor circuit board and the sensor housing.

Embodiment 19: The incubator of Embodiment 18, further comprising a skin sensor connection assembly electrically connected to the sensor circuit board, a portion of the skin sensor connection assembly connected to the sensor circuit board also encapsulated in the fill material.

Embodiment 20: The incubator of Embodiment 18, wherein the fill material is a resin material that protects the sensor circuit board when the skin sensor is boiled in water.

In at least some exemplary embodiments, the exemplary disclosed system, apparatus, and method may provide an efficient and effective system for providing infant incubation in facilities or areas having unreliable electrical power access. Also, the exemplary disclosed system, apparatus, and method may provide an efficient and effective system for providing infant incubation in facilities or areas having relatively unsanitary conditions. The exemplary disclosed system, apparatus, and method may be manufactured at a significantly lower cost than typical incubators designed for developed world hospital use.

It will be apparent to those skilled in the art that various modifications and variations can be made to the exemplary disclosed system, apparatus, and method. Other embodiments will be apparent to those skilled in the art from consideration of the specification and practice of the exemplary disclosed apparatus, system, and method. It is intended that the specification and examples be considered as exemplary, with a true scope being indicated by the following claims.

What is claimed is:

1. An incubator, comprising:

an insulated housing that forms an incubation chamber;

a plurality of recirculating heating airflow passages configured to draw a heating airflow from the incubation chamber, heat the heating airflow based on being heated by a heating component, and return the heating airflow to the incubation chamber;

a plurality of ventilation airflow passages configured to draw a ventilation airflow from outside of the incubator and into the incubation chamber, and vent the ventilation airflow out of the incubation chamber; and a heating fan of the plurality of recirculating heating airflow passages, and a ventilation fan of the plurality of ventilation airflow passages;

wherein the plurality of recirculating heating airflow passages are separate from the plurality of ventilation airflow passages so that the heating airflow is separated from the ventilation airflow when the heating airflow is in the plurality of recirculating heating airflow passages and the ventilation airflow is in the plurality of ventilation airflow passages; and wherein the heating airflow and the ventilation airflow both flow through the incubation chamber.

2. The incubator of claim 1, wherein the heating component includes metal wiring wrapped around a heat exhaust passage of the plurality of recirculating heating airflow passages disposed upstream of the incubation chamber and configured to heat the heating airflow returning to the incubation chamber.

3. The incubator of claim 1, further comprising a replaceable screw-in air filter disposed in the plurality of ventilation airflow passages upstream of the incubation chamber and configured to filter the ventilation airflow entering the incubation chamber.

4. The incubator of claim 1, further comprising a mosquito screen of a ventilation air intake of the plurality of ventilation airflow passages configured to draw the ventilation airflow from outside of the incubator.

5. The incubator of claim 1, further comprising a mass flow sensor integrated into a ventilation air intake of the plurality of ventilation airflow passages configured to draw the ventilation airflow from outside of the incubator.

6. The incubator of claim 1, further comprising a touchscreen configured to receive input for a controller that controls the heating fan of the plurality of recirculating heating airflow passages and the ventilation fan of the plurality of ventilation airflow passages.

7. The incubator of claim 6, wherein the touchscreen, the controller, the heating fan, and the ventilation fan are all configured to be powered by a a single 12V lead-acid battery.

8. An incubator, comprising:

an insulated housing that forms an incubation chamber;

a plurality of recirculating heating airflow passages configured to draw a heating airflow from the incubation chamber, heat the heating airflow based on being heated by a heating component, and return the heating airflow to the incubation chamber;

a plurality of ventilation airflow passages configured to draw a ventilation airflow from outside of the incubator and into the incubation chamber, and vent the ventilation airflow out of the incubation chamber; and a heating fan of the plurality of recirculating heating airflow passages, and a ventilation fan of the plurality of ventilation airflow passages;

wherein the plurality of recirculating heating airflow passages are separate from the plurality of ventilation airflow passages so that the heating airflow is separated from the ventilation airflow when the heating airflow is in the plurality of recirculating heating airflow passages and the ventilation airflow is in the plurality of ventilation airflow passages; and wherein the heating airflow and the ventilation airflow only come together in the incubation chamber when in the incubator.

9. The incubator of claim 8, wherein the heating component includes metal wiring wrapped around a heat exhaust passage of the plurality of recirculating heating airflow passages disposed upstream of the incubation chamber and configured to heat the heating airflow returning to the incubation chamber.

10. The incubator of claim 8, further comprising a replaceable screw-in air filter disposed in the plurality of ventilation airflow passages upstream of the incubation chamber and configured to filter the ventilation airflow entering the incubation chamber.

11. The incubator of claim 8, further comprising a mosquito screen of a ventilation air intake of the plurality of ventilation airflow passages configured to draw the ventilation airflow from outside of the incubator.

12. The incubator of claim 8, further comprising a mass flow sensor integrated into a ventilation air intake of the plurality of ventilation airflow passages configured to draw the ventilation airflow from outside of the incubator.

13. The incubator of claim 8, further comprising a touchscreen configured to receive input for a controller that controls the heating fan of the plurality of recirculating heating airflow passages and the ventilation fan of the plurality of ventilation airflow passages.

14. The incubator of claim 13, wherein the touchscreen, the controller, the heating fan, and the ventilation fan are all configured to be powered by a single 12V lead-acid battery.

15. An incubator, comprising:

an insulated housing that forms an incubation chamber;

a plurality of recirculating heating airflow passages configured to draw a heating airflow from the incubation chamber, heat the heating airflow based on being heated by a heating component, and return the heating airflow to the incubation chamber;

a plurality of ventilation airflow passages configured to draw a ventilation airflow from outside of the incubator and into the incubation chamber, and vent the ventilation airflow out of the incubation chamber; and a heating fan of the plurality of recirculating heating airflow passages, and a ventilation fan of the plurality of ventilation airflow passages;

wherein the plurality of recirculating heating airflow passages are separate from the plurality of ventilation airflow passages so that the heating airflow is separated from the ventilation airflow when the heating airflow is in the plurality of recirculating heating airflow passages and the ventilation airflow is in the plurality of ventilation airflow passages;

wherein the heating airflow and the ventilation airflow both flow through the incubation chamber; and wherein the heating fan and the ventilation fan are both configured to be powered by a single 12V lead-acid battery.

16. The incubator of claim 15, wherein the heating component includes metal wiring wrapped around a heat exhaust passage of the plurality of recirculating heating airflow passages disposed upstream of the incubation chamber and configured to heat the heating airflow returning to the incubation chamber.

17. The incubator of claim 15, further comprising a replaceable screw-in air filter disposed in the plurality of ventilation airflow passages upstream of the incubation chamber and configured to filter the ventilation airflow entering the incubation chamber.

18. The incubator of claim 15, further comprising a mosquito screen of a ventilation air intake of the plurality of ventilation airflow passages configured to draw the ventilation airflow from outside of the incubator.

19. The incubator of claim 15, further comprising a mass flow sensor integrated into a ventilation air intake of the plurality of ventilation airflow passages configured to draw the ventilation airflow from outside of the incubator.

20. The incubator of claim 15, further comprising a touchscreen configured to receive input for a controller that controls the heating fan of the plurality of recirculating heating airflow passages and the ventilation fan of the plurality of ventilation airflow passages.

* * * * *